(12) United States Patent
Chirgadze et al.

(10) Patent No.: US 6,271,227 B1
(45) Date of Patent: Aug. 7, 2001

(54) ANTITHROMBOTIC AGENTS

(75) Inventors: Nickolay Y Chirgadze, Carmel; Matthew J Fisher, Mooresville; Richard W Harper, Indianapolis; Ho-Shen Lin, Indianapolis; Jefferson R McCowan, Indianapolis; Alan D Palkowitz, Carmel; Michael E Richett, Indianapolis; Daniel J Sall, Greenwood; Gerald F Smith, Indianapolis; Kumiko Takeuchi, Indianapolis, all of IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,124

(22) PCT Filed: Apr. 30, 1998

(86) PCT No.: PCT/US98/08831

§ 371 Date: Jan. 24, 2000

§ 102(e) Date: Jan. 24, 2000

(87) PCT Pub. No.: WO98/49160

PCT Pub. Date: Nov. 5, 1998

Related U.S. Application Data

(60) Provisional application No. 60/044,296, filed on Apr. 30, 1997.

(51) Int. Cl.$^7$ .................. A61K 21/5377; A61P 7/02; C07D 413/14
(52) U.S. Cl. .................. 514/233.5; 544/141; 548/311.4; 548/454; 548/523; 548/525
(58) Field of Search .................. 544/141; 548/525; 514/233.5

(56) References Cited

U.S. PATENT DOCUMENTS

| | | |
|---|---|---|
| 3,274,213 | 9/1966 | Lednicer . |
| 3,293,263 | 12/1966 | Lednicer . |
| 4,001,426 | 1/1977 | Brenner et al. . |
| 4,007,204 | 2/1977 | Descamps et al. . |
| 4,133,814 | 1/1979 | Jones et al. . |
| 4,418,068 | 11/1983 | Jones et al. . |
| 5,441,965 | 8/1995 | Sall et al. . |
| 5,472,962 | 12/1995 | Koizumi et al. . |
| 5,510,357 | 4/1996 | Palkowitz . |
| 5,523,309 | 6/1996 | Bryant et al. . |
| 5,532,254 | 7/1996 | Bowling . |
| 5,552,401 * | 9/1996 | Cullinan ................ 544/141 |
| 5,567,828 | 10/1996 | Dodge et al. . |
| 5,576,343 | 11/1996 | Nagahara et al. . |

FOREIGN PATENT DOCUMENTS

| | | |
|---|---|---|
| 0 617030 | 9/1994 | (EP) . |
| 0 716 855 | 6/1996 | (EP) . |
| WO 95/10513 | 4/1995 | (WO) . |
| WO 95/17095 | 6/1995 | (WO) . |
| WO 95/17382 | 6/1995 | (WO) . |
| WO 96/11677 | 4/1996 | (WO) . |
| WO 97/25033 | 7/1997 | (WO) . |

OTHER PUBLICATIONS

Robert M. Scarborough, "Chapter 8. Anticoagulant Strategies Targeting Thrombin and Factor Xa," *Annual Reports in Medicinal Chemistry*, (1995) 30, pp. 71–80.

Bastian, et al., "Preparation of [(pyrrolidinoalkoxy)pheyl]–benzothiophenes and analogs as thrombin inhibitors," *Chemical Abstracts*, vol. 127, No. 3 (1997).

Sall, et al., Dibasic benzo[b] thiophene derivatives as a novel class of active site–directed thrombin inhibitors. 1. Determination of the serine protease selectivity, structure–activity relationships, and binding orientation, *J. Med. Chem.*, vol. 40, No. 22, Oct. 24, 1997.

Jones, C., et al., *J. Med. Chem.*, 22 (8), 966–966 (1979).

Jones, C., et al., *J. Med. Chem*, 27 (8), 1057–1066 (1984).

Delgado and Remens, *Textbook of Organic Medicinal and Pharmaceutical Chemistry*, 9$^{th}$ Edition, 30–31 (1991).

Green and Wuts, *Protective Groups in Organic Syntnesis*, 2$^{nd}$ Edition, 77–79 (1991).

Kauffman, et al., "Selective Estrogen Receptor Modulators," *Drug News and Perspectives*, vol. 8, No. 9, 531–539, XP002055053 (1995).

Grese, et al., "Structure–Activity Relationships of Selective Estrogen Receptor Modulators: Modifications to the 2–Arylbenzothiophene Core of Raloxifene," *Journal of Medicinal Chemistry, US, American Chemical Society*, vol. 40, No. 2, 146–167, XP002050782 (1997).

Richet, et al., "Synthesis and In Vitro Evaluation of Novel Series of Potent Benzothiophene–Derived Thrombin Inhibitors," *Abstracts of Papers*, Part 1, ACS National Meeting, 214$^{th}$ XP000881570 (1997).

\* cited by examiner

Primary Examiner—Robert W. Ramsuer
(74) Attorney, Agent, or Firm—Arvie J. Anderson; Thomas E. Jackson

(57) ABSTRACT

This application relates to novel compounds of formula (I) (and their pharmaceutically acceptable salts), as defined herein, processes and intermediates for their preparation, pharmaceutical formulations comprising the novel compounds of formula (I), and the use of the compounds of formula (I) as thrombin inhibitors.

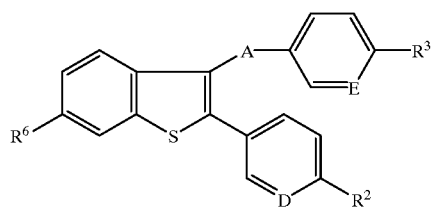

47 Claims, No Drawings

ANTITHROMBOTIC AGENTS

This application claim benefit to provisional application 60/044,296 filed Apr. 30, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

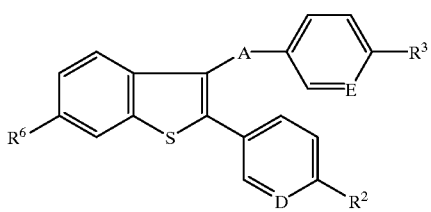

wherein
  A is carbonyl or methylene;
  D is CH, $CR^d$ or N in which $R^d$ is methyl or methoxy;
  E is CH, $CR^e$ or N in which $R^e$ is methyl, methoxy or halo;
  $R^2$ and $R^3$ are defined together such that
  A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and
    $R^3$ is $-CH_2-R^c$, in which $R^c$ is 2-carboxypyrrolidin-1-yl or 2-[[(1–4C)alkoxy]carbonyl]pyrrolidin-1-yl; or
  B. $R^2$ is $-X^2-(CH_2)_n-R^f$ in which $X^2$ is a direct bond, methylene or O; n is 1, 2 or 3; provided that when n is 1, then $X^2$ is a direct bond; and $R^f$ is 2-carboxypyrrolidin-1-yl, 2-[[(1–4C)alkoxy]carbonyl]pyrrolidin-1-yl, (carboxymethyl)amino, [[(1–4C)alkoxy]carbonylmethyl]amino, (4-carbonylmethylimidazol-1-yl)amino, [4-[[(1–4C)alkoxyl]-carbonylmethyl]imidazol-1-yl]amino, [4-carboxybenzyl)amino, [4-[[(1–4C)alkoxy]carbonyl]benzyl]amino, (3-amino-1,4-dioxo-4-hydroxybutyl)amino or [3-amino-1,4-dioxo-4-[(1–4C)alkoxy]-butyl]amino; or
    $R^2$ is $-X^2-(CH_2)_n-R^f$ in which $X^2$ is a direct bond; n is 0; and $R^f$ is (3-amino-1,4-dioxo-4-hydroxybutyl)-amino, [3-amino-1,4-dioxo-4-[(1–4C)alkoxy]butyl]amino, (4-amino-1,5-dioxo-5-hydroxypentyl)amino or [4-amino-1,5-dioxo-5-[(1–4C)alkoxy]butyl]amino;
  $R^3$ is is $-X^3-(CH_2)_s-NR^gR^h$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and
  $R^6$ is hydrogen, hydroxy or methoxy.

A particular thrombin inhibiting compound of formula I (or a pharmaceutically acceptable salt thereof) is one wherein
  A is carbonyl or methylene;
  D is CH, $CR^d$ or N in which $R^d$ is methyl or methoxy;
  E is CH, $CR^e$ or N in which $R^e$ is methyl, methoxy or halo;
  $R^2$ and $R^3$ are defined together such that
  A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and
    $R^3$ is $-CH_2-R^c$, in which $R^c$ is 2-carboxypyrrolidin-1-yl or 2-[[(1–4C)alkoxy]carbonyl]pyrrolidin-1-yl; or
  B. $R^2$ is $-X^2-(CH_2)_n-R^f$ in which $X^2$ is a direct bond, methylene or O; n is 1 or 2; provided that when n is 1, then $X^2$ is a direct bond; and $R^f$ is 2-carboxypyrrolidin-1-yl, 2-[[(1–4C)alkoxy]carbonyl]pyrrolidin-1-yl, (carboxymethyl)-amino, [[(1–4C)alkoxy]carbonylmethyl]amino, (4-carboxymethylimidazol-1-yl)amino, [4-[[(1–4C)

alkoxy]carbonylmethyl]imidazol-1-yl]amino, (4-carboxybenzyl)amino, [4-[[(1–4C)alkoxy]carbonyl]benzyl]amino, (3-amino-1,4-dioxo-4-hydroxybutyl)amino or [3-amino-1,4-dioxo-4-[(1–4C)alkoxy]-butyl]amino; and $R^3$ is is —$X^3$—$(CH_2)_s$—$NR^gR^h$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^6$ is hydrogen, hydroxy or methoxy.

A particular value for D is CH.

A particular value for E is CH or $CR^e$ in which $R^e$ is methyl or methoxy.

One particular set of values for $R^2$ and $R^3$ defined together is $R^2$ is —$X^2$—$(CH_2)_m$—$NR^aR^b$ in which $X^2$ is a direct bond or O; m is 2; and the group $NR^aR^b$ is pyrrolidino; and $R^3$ is —$CH_2$—$R^c$, in which $R^c$ is 2-carboxypyrrolidin-1-yl.

Another particular set of values for $R^2$ and $R^3$ defined together is $R^2$ is —$X^2$—$(CH_2)_n$—$R^f$ in which $X^2$ is a direct bond or O; n is 2; and $R^f$ is 2-carboxypyrrolidin-1-yl or 2-[[(1–4C)alkoxy]carbonyl]pyrrolidin-1-yl (and more particularly, the (1–4C)alkoxy is t-butoxy); and $R^3$ is pyrrolidinomethyl, morpholinomethyl or 2-pyrrolidinoethoxy.

A further particular set of values for $R^2$ and $R^3$ defined together is $R^2$ is —$X^2$—$(CH_2)_n$—$R^f$ in which $X^2$ is a direct bond; n is 0; and $R^f$ is (3-amino-1,4-dioxo-4-hydroxy-butyl)amino or (4-amino-1,5-dioxo-5-hydroxypentyl)amino; and $R^3$ is pyrrolidinomethyl, morpholinomethyl or 2-pyrrolidinoethoxy.

A particular value for $R^6$ is hydroxy.

A particular value for A is methylene.

A preferred method of the invention includes one wherein said compound of formula I is one of those described herein at Examples 2, 3 and 10.

Another preferred method of the invention is one wherein said compound of formula I is one of those described herein at Examples 19 and 20, particularly Example 19.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorders.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

In general, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel. A pharmaceutically acceptable salt of an antithrombotic diamine of the instant invention includes one which is an acid-addition salt made with an acid which provides a pharmaceutically acceptable anion. Thus, an acid addition salt of a novel compound of formula I as provided above made with an acid which affords a pharmaceutically acceptable anion provides a particular aspect of the invention. Examples of such acids are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–4C)alkoxy group is methoxy, ethoxy, isopropoxy or t-butoxy, and more particularly, t-butoxy.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, and described in the examples, in which each of $Q^2$, $Q^3$ and $Q^6$, respectively, represents a value defined for the groups $R^2$, $R^3$ and $R^6$, a protected version of such a group, or moiety which can be further elaborated into such a group. Final conversion of a group $Q^2$, $Q^3$ or $Q^6$ into $R^2$, $R^3$ or $R^6$ is carried out at a convenient point, consistent with the chemistry employed. It will be recognized that a number of other routes may be used, particularly those involving condensation of an organometallic species to form a compound of formula C or G in Scheme I.

salt thereof) as provided in any of the above descriptions which is selected from any of those described in the examples, including, (a) for a compound of formula I in which $R^c$ is 2-[[(1–4C)alkoxy]carbonyl]pyrrolidin-1-yl, alkylating 2-[[(1–4C)alkoxy]carbonyl]pyrrolidine using a compound corresponding to a compound of formula I but in which $R^c$ is a leaving group, for example a methylsulfonyloxy group as described in Example 9-E;

(b) for a compound of formula I in which $R^2$ is —$X^2$—$(CH_2)_n$—$R^f$ in which n is not 0 and the atom joining $R^f$ to —$X^2$—$(CH_2)_n$— is a basic nitrogen, alkylating a corresponding amine of formula H-$R^f$ using a compound corresponding to a compound of formula I but in which $R^f$ is a leaving group, for example a methylsulfonyloxy group as described in Example 1-C;

(c) for a compound of formula I in which $R^2$ is —$X^2$—$(CH_2)_n$—$R^f$ in which n is not 0 and the atom joining $R^f$ to —$X^2$—$(CH_2)_n$— is a basic imino group joined to a methylene group (—NH—$CH_2$—) [i.e. $R^f$ is (carboxymethyl)

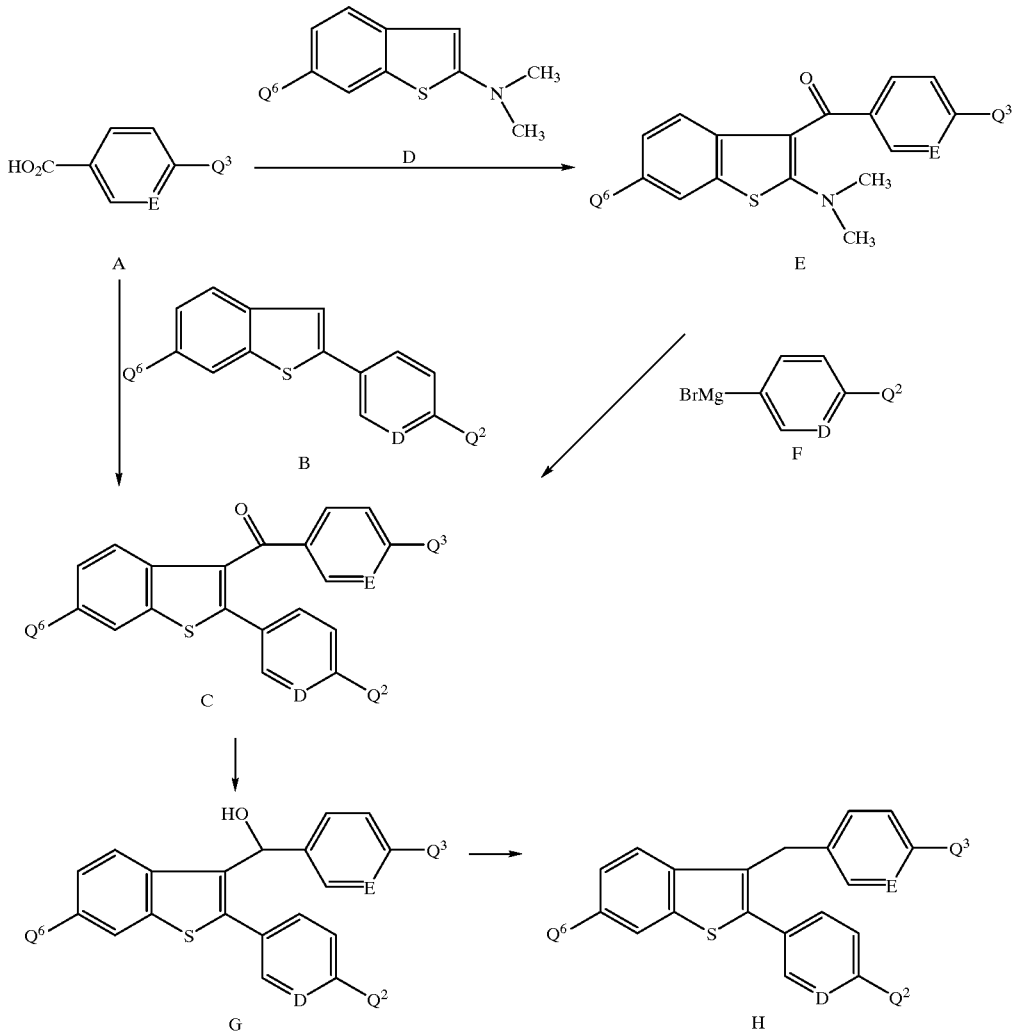

Scheme I

Thus, there is provided a process for preparing a novel compound of formula I (or a pharmaceutically acceptable salt amino, [[(1–4C)alkoxy]carbonylmethyl]amino, (4-carboxybenzyl)amino, or [4-[[(1–4C)alkoxy]carbonyl]

benzyl]amino], reductively alkylating a compound corresponding to a compound of formula I but in which $R^f$ is an amino group using the requisite aldehyde, for example as described in Example 12;

(d) for a compound of formula I in which $R^2$ is $-X^2-(CH_2)_n-R^f$ in which n is not 0 and the atom joining $R^f$ to $-X^2-(CH_2)_n-$ is an amide nitrogen, acylating a compound corresponding to a compound of formula I but in which $R^f$ is an amino group using the requisite acid or an activated derivative thereof, for example by coupling using a carbodiimide reagent as described in Example 18;

(e) for a compound of formula I in which $R^2$ is $-X^2-(CH_2)_n-R^f$ in which n is 0, acylating a compound corresponding to a compound of formula I but in which $R^2$ is an amino group using the requisite acid or an activated derivative thereof, for example by coupling using a carbodiimide reagent as described in Example 19;

(f) for a compound of formula I in which $R^2$ or $R^3$ contains a carboxy group, decomposing the ester of a corresponding compound of formula I in which $R^2$ or $R^3$ contains a [(1–4C)alkoxy]carbonyl group, for example using the acid catalyzed decomposition of a t-butyl ester as described in Example 2 or an acid or base catalyzed hydrolysis as described in Example 11-D or Example 13;

(g) for a compound of formula I in which A is methylene, reductively removing the hydroxy group of a corresponding alcohol of formula II, for example using a procedure analogous to that of Example 3-A;

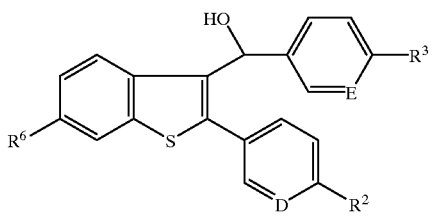

II whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction). An activated derivative of a carboxylic acid includes, for example, an ester (such as a methyl ester), an acid halide (such as an acid chloride), an activated ester (such as with 1-hydroxybenzotriazole or N-hydroxysuccinimide), an anhydride with a carboxylic acid (such as by formed by reaction with butyl chloroformate) or an activated derivative formed by reaction with a coupling reagent (such as with a carbodiimide, for example with dicyclohexylcarbodiimide or with 1-(3-dimethyaminopropyl)-3-ethylcarbodiimide).

Novel intermediate or starting material compounds, such as an alcohol of formula II provide a further aspect of the invention. As noted above, an alcohol of formula II may be obtained by reduction of the carbonyl of a corresponding compound of formula I or by condensation of an organometallic species with the requisite aldehyde.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which $R^6$ which is hydroxy, but in which the corresponding substituent is $-OR^P$ in place of hydroxy, wherein $R^P$ is a phenol protecting group other than methyl. Phenol protecting groups are well known in the art, for example as described in T. W. Greene and P. G. M. Wuts, "Protecting Groups in Organic Synthesis" (1991). Particular values of $R^P$ include, for example, benzyl and allyl. Further, $R^P$ may denote a functionalized resin, for example as disclosed in H. V. Meyers, et al., *Molecular Diversity*, (1995), 1, 13–20.

As mentioned above, the invention includes pharmaceutically acceptable salts of the Lhrombin inhibiting compounds defined by the above formula I. A particular compound of this invention possesses one or more sufficiently basic functional groups to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those corresponding to a compound of formula I but in which $R^6$ is -ORP discussed above. Selective methods for cleavage of methyl ethers, as described in the examples, are discussed in Jones, et al., *J. Med. Chem.,* (1984), 27, 1057–1066. For example, the diether 3-(4-methoxybenzoyl)-2-(4-methoxyphenyl)benzo[b]thiophene may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide affords the isomeric monoether 3-(4-hydroxybenzoyl)-2-(4-methoxyphenyl)benzo[b]thiophene. Treatment with boron tribromide under less mild conditions (0°, 6 hours) or with aluminum chloride and ethanethiol cleaves both ethers.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:
Active ingredient 100 mg
Isotonic saline 1,000 mL The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 μL buffer (0.03M Tris, 0.15M NaCl, pH 7.4) with 25 μL of human thrombin solution (purified human thrombin, Enzyme Research Laboratories, South Bend, Ind., at 8 NIH units/mL) and 25 μL of test compound in a solvent (50% aqueous methanol (v:v)). Then 150 μL of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

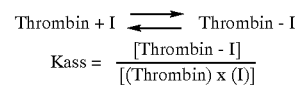

$$\text{Kass} = \frac{[\text{Thrombin - I}]}{[(\text{Thrombin}) \times (\text{I})]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Indiana; human urokinase from Leo Pharmaceuticals, Denmark; and recombinant activated Protein C (aPC) is prepared at Eli Lilly and Co. substantially according to U.S. Pat. No 4,981, 952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See,. Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 $\mu$mol/kg/h.

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.,* 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human Fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.,* 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL, in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\ po}{AUC\ iv} \times \frac{\text{Dose } iv}{\text{Dose } po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/− SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, $t_{0.5}$; and area under the curve, A.U.C.; fraction of test compound absorbed, F.

Canine Model of Coronary Artery Thrombosis

Surgical preparation and instrumentation of the dogs are as described in Jackson, et al., *Circulation,* 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood PO$_2$, PCO$_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
Bn or Bzl=benzyl
Bu=butyl
n-BuLi=butyllithium
calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
Et$_3$N=triethylamine
Et$_2$O=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NES=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
SiO$_2$=silica gel
SM=starting material
TBS=tert-butyldimethylsilyl
TEA=triethylamine
Temp.=temperature
TFA=trifluoroacetic acid THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (™)" silica cartridges; radial chromatography indicates preparative chromatography using a "Chromatotron (™)" instrument.

EXAMPLE 1

Preparation of 2-[4-[2-[2-(S)-(tert-Butoxycarbony)pyrroidin-1-yl]ethyloxy]phenyl]-6-(hydroxy)benzo[b]thiophen-3-yl 3-Methoxy-4-[(4-morpholinyl)methyl]phenyl Ketone Dioxalate

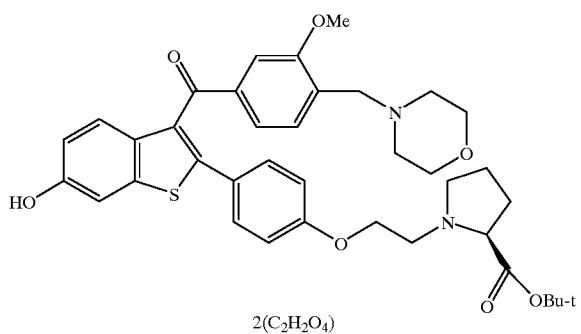

A. 2-(4-Bromophenoxy) ethyl Triisopropylsilyl Ether

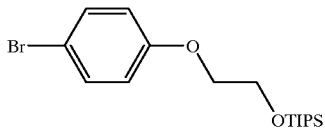

Triisopropylsilyl trifluoromethanesulfonate (24.4 mL, 90.7 mmol) was added to a stirred solution of 2-(4-bromophenoxy)ethanol (15.1 g, 69.8 mmol) and anhydrous triethylamine (19.4 mL, 140 mmol) in anhydrous $CH_2Cl_2$ (30 mL) at 0° C. under nitrogen atmosphere. The resultant mixture was stirred for 1 h. The mixture was washed with saturated $NaHCO_3$ (25 mL), extracted with EtOAc (3×75 mL), dried over $MgSO_4$, filtered, concentrated, and chromatographed on silica (10% $CH_2Cl_2$ in hexanes) to give 23.4 g (90%) of the silyl ether as a colorless liquid.

IR (thin film) 2944, 1489 $cm^{-1}$; FDMS m/e 372 ($M^+$, $^{79}Br$) and 374 ($M^+$, $^{81}Br$). Anal. Calcd. for $C_{17}H_{29}BrO_2Si$: C, 54.68; H, 7.83. Found: C, 54.97; H, 7.55.

B. 6-Benzyloxy-2-[4-[2-(hydroxy)ethoxy]phenyl]-benzo[b]thiophen-3-yl 3-Methoxy-4-[(4-morpholinyl)methyl]-phenyl Ketone

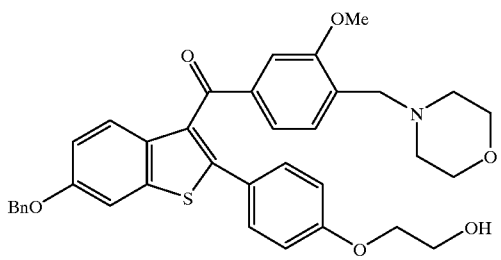

The above silyl ether (2.71 g, 7.26 mmol) was added to a stirred suspension of magnesium ribbons (164 mg, 6.77 mmol) in anhydrous THF (4 mL) under argon atmosphere, followed by the addition of a small iodine chip. The resultant mixture was heated in an oil bath at 60–65° C. for 1.5 h to form a homogeneous Grignard solution. The Crignard solution was cooled to room temperature and diluted with anhydrous THF (10 mL) before it was added to a stirred solution of 6-benzyloxy-2-(dimethylamino)benzo[b]thiophen-3-yl 3-methoxy-4-[(4-morpholinyl)methyl]phenyl ketone (2.50 g, 4.84 mmol) in anhydrous THF (10 mL) at 0° C. under argon atmosphere. The resultant mixture was stirred at 0° C. for 1.5 h, then quenched with saturated aqueous $NH_4Cl$ (15 mL). After extraction with EtOAc (70 mL×2), the combined organic layers were dried over $MgSO_4$, filtered, and concentrated to give a gummy residue which was dissolved in anhydrous THF (25 mL) and treated with tetrabutylammonium fluoride (5.80 mL, 1 M in THF) at room temperature under nitrogen atmosphere. After stirring for 1 h, the mixture was concentrated under vacuum; the residue was chromatographed on silica [gradient 0–30% $MeOH/Et_3N$ (2/1) in EtOAc] to give 2.61 g (88%) of the keto alcohol as a foam.

IR (neat) 3426 (br), 1646, 1605 $cm^{-1}$; FDMS m/e 609 ($M^+$); Anal. Calcd. for $C_{36}H_{35}NO_6S$: C, 70.91; H, 5.79; N, 2.30. Found: C, 70.63; H, 5.65; N, 2.04.

C. 6-Benzyloxy-2-[4-[2-[2-(S)-(tert-butoxycarbonyl)-pyrrolidin-1-yl]ethoxy]phenyl]benzo[b]thiophen-3-yl 3-Methoxy-4-[(4-morpholinyl)methyl]phenyl Ketone

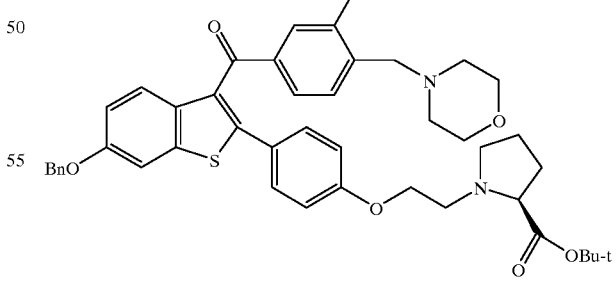

Anhydrous triethylamine (1.05 mL, 7.53 mmol) and methanesulfonyl chloride (0.233 mL, 3.01 mmol) were sequentially added to a stirred solution of the above keto alcohol (1.53 g, 2.51 mmol) in anhydrous dichloromethane (15 mL) at 0° C. under nitrogen atmosphere, the reaction mixture was allowed to stir at 0° C. for 1.5 h. After dilution with EtOAc (60 mL), the mixture was washed with water (20 mL×2), dried, filtered, and concentrated to give a 1.73 g (100%) of the desired mesylate as a foam.

(L)-Proline t-butyl ester (0.190 mL, 1.16 mmol) and anhydrous triethylamine (0.25 mL) were added to a stirred solution of the mesylate (320 mg, 0.465 mmol) in dry DMF (2 mL). The resultant mixture was heated at 70° C. for 36 h. At room temperature, the mixture was diluted with EtOAc (30 mL), washed with water (10 mL×2), dried over $MgSO_4$, filtered, concentrated, and chromatographed on silica [gradient 0–5% $EtOH/Et_3N$ (2/1) in EtOAc] to give 255 mg (72%) of the keto ester as a foam.

IR (neat) 1727, 1647, 1605 $cm^{-1}$; FDMS m/e 762 ($M^+$).

D. 2-[4-[2-[2-(S)-(tert-Butoxycarbonyl)pyrrolidin-1-yl]-ethyloxy]phenyl]-6-(hydroxy)benzo[b]thiophen-3-yl 3-Methoxy-4-[(4-morpholinyl)methyl]phenyl Ketone Dioxalate

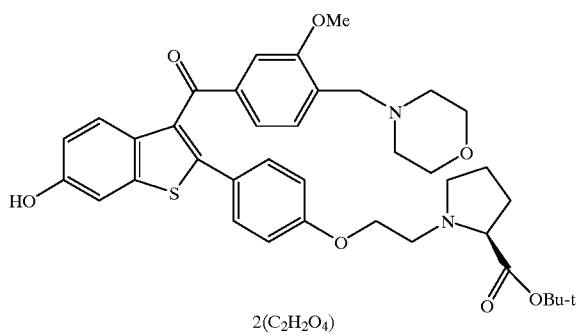

To a stirred solution of the above benzyloxy ester (75 mg, 0.098 mmol) in THF (3 mL) under nitrogen atmosphere were sequentially added 10% Pd/C (75 mg) and 25% aqueous $HCO_2NH_4$ (0.4 mL). The resultant mixture was stirred under a balloon nitrogen atmosphere for 6 h. After filtration, the filtrate was diluted with EtOAc, washed with half-saturated NaCl, dried over $MgSO_4$, filtered, concentrated, and chromatographed on silica [gradient 0–5% $EtOH/Et_3N$ (2/1) in EtOAc] to give 50 mg (76%) of the hydroxy-ester as a foam.

A solution of oxalic acid (50 mg, 0.074 mmol) in EtOAc (3 mL) was added dropwise to a stirred solution of the hydroxy-ester (13.4 mg, 0.148 mmol) in EtOAc (3 mL). The resultant white suspension was filtered and the white solid was dried at 60° C. under vacuum to provide compound the salt (38 mg) as a yellowish solid in an overall 46% yield from the above benzyloxy ester.

IR (KBr) 3400–2500 (br), 1733, 1640, 1606 $cm^{-1}$; FDMS m/e 673 ($M^++1-2[C_2H_2O_4]$); Anal. Calcd. for $C_{38}H_{44}N_2O_7S.2(C_2H_2O_4)$: C, 59.15; H, 5.67; N, 3.28. Found: C, 58.94; H, 5.70; N, 3.48.

The 6-benzyloxy-2-(dimethylamino)benzo[b]thiophen-3-yl 3-methoxy-4-[(4-morpholinyl)methyl]phenyl ketone used in part B, above, may be obtained using a method similar to that described in Example 9-A, below, but using 3-methoxy-4-(4-morpholinyl)benzoic acid hydrochloride. The benzoic acid may be obtained in a manner similar to the preparation described in Example 5 for 3-methoxy-4-(1-pyrrolidinyl)-benzoic acid hydrochloride.

EXAMPLE 2

Preparation of 6-Hydroxy-2-[4-[2-[2-(S)-(carboxy) pyrrolidin-1-yl]ethoxy]phenyl]benzo[b]thiophen-3-yl 3-Methoxy-4-[(4-morpholinyl)methyl]phenyl Ketone Dioxalate.

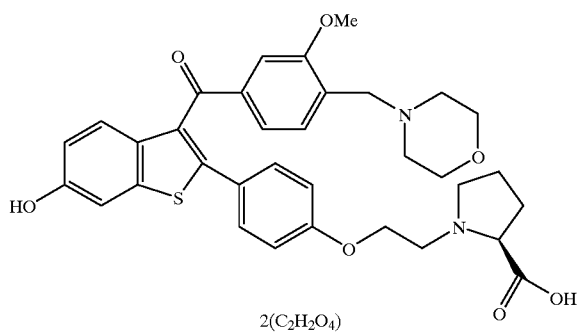

Trifluoroacetic acid (3 mL) was added to a stirred solution of the keto ester of Example 1 (230 mg, 0.342 mmol) in anhydrous 1,2-dichloroethane (3 mL) at 0° C. under nitrogen atmosphere. The resultant solution was stirred at room temperature for 6 h. After concentration, the gummy residue was dissolved in THF (4 mL), and the solution was stirred and treated with a solution of oxalic acid (90 mg) in THF/EtOAc (2 mL/2 mL) to form a suspension. An additional 5 mL of EtOAc was added to the suspension. After filtration and subsequent drying under vacuum at 50° C., 190 mg (70w) of the keto acid was obtained as a yellowish solid.

IR (KBr) 3400–2500 (br), 1726, 1641, 1606 $cm^{-1}$; FDMS m/e 617 ($M^++1-2[C_2H_2O_4]$); Anal. Calcd. for $C_{34}H_{36}N_2O_7S.1.9(C_2H_2O_4)$: C, 57.63; H, 5.09; N, 3.56. Found: C, 57.63; H, 4.98; N, 3.66.

EXAMPLE 3

Preparation of 2-[4-[2-[2-(S)-(tert-Butoxycarbonyl)-pyrrolidin-1-yl]ethoxy]phenyl]-6-hydroxy-3-[3-methoxy-4-[(4-morpholinyl)methyl3benzyl]benzo[b] thiophene

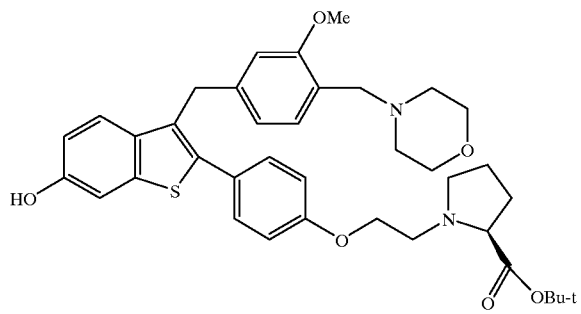

A. 6-Benzyloxy-2-[4-[2-(hydroxy)ethyloxy]phenyl]-3-[3-methoxy-4-[(4-morpholinyl)methyl]benzyl]benzo[b]thiophene

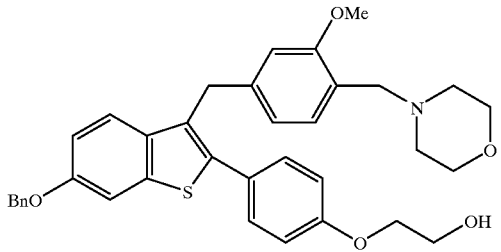

DIBAL-H (5.58 mL, 1 M in toluene) was added to a stirred solution of the keto alcohol of Example 1-B (1.36 g, 2.23 mmol) in anhydrous $CH_2Cl_2$ (10 mL) at 0° C. under nitrogen atmosphere, the resultant solution was stirred at 0° C. for 50 min. The reaction mixture was treated sequentially with MeOH (1 mL) and saturated aqueous Rochelle's salt solution (20 mL), and the two-layered solution was stirred vigorously at room temperature for 1.5 h. After extraction with EtOAc, the organic layer was dried over $MgSO_4$, filtered, and concentrated to yield the diol.

The above diol was dissolved in anhydrous $CH_2Cl_2$ (15 mL) and cooled down to 0° C. before it was sequentially treated with $Et_3SiH$ (2.49 mL, 15.6 mmol) and TFA (1.72 mL, 22.3 mmol). The resultant mixture was stirred at 0° C. for 1 h. After cautious treatment with saturated aqueous $NaHCO_3$ to neutralize TFA, the mixture was allowed to warm to room temperature where it was extracted with EtOAc (60 mL). The combined organic layers were dried over $MgSO_4$, filtered, concentrated, and chromatographed on silica [gradient 0–5% $EtOH/Et_3N$ (2/1) in EtOAc] to give compound the alcohol as a foam (1.05 g) in an overall 79% yield from the keto alcohol.

IR (KBr) 3405 (br), 1608 $cm^{-1}$; FDMS m/e 595 $M^+$); Anal. Calcd. for $C_{36}H_{37}NO_5S$: C, 72.58; H, 6.26; N, 2.35. Found: C, 72.87; H, 6.29; N, 2.27.

B. 6-Benzyloxy-2-[4-[2-[2-(S)-(tert-butoxycarbonyl)-pyrrolidin-1-yl]ethoxy]phenyl]-3-[3-methoxy-4-[(4-morpholinyl)methyl]benzyl]benzo[b]thiophene

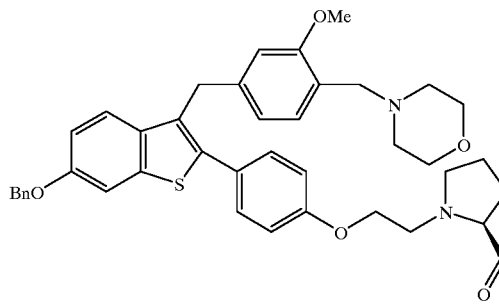

Following the procedure described in Example 1-C, the benzyloxy ester was obtained from the above alcohol as a foam in an overall 100% yield.

IR (neat) 1736, 1608 $cm^{-1}$; FDMS m/e 749 ($M^++1$).

C. 2-[4-[2-[2-(S)-(tert-Butoxycarbonyl)pyrrolidin-1-yl]-ethoxy]phenyl]-6-hydroxy-3-[3-methoxy-4-[(4-morpholinyl)-methyl]benzyl]benzo[b]thiophene Following the debenzylation procedure described in Example 1-D, the hydroxy ester was obtained from the above benzyloxy ester as a foam in a 89% yield.

IR (neat) 3200 (br), 1732, 1608 $cm^{-1}$; FDMS m/e 659 ($M^++1$); Anal. Calcd. for $C_{38}H_{46}N_2O_6S$: C,69.27; H,7.04; N,4.25. Found: C,69.44; H,7.16; N,4.52.

EXAMPLE 4

Preparation of 6-Hydroxy-2-[4-[2-[2-(S)-(carboxy)pyrrolidin-1-yl]ethoxy]phenyl]-3-[3-methoxy-4-[(4-morpholinyl)methyl]-benzyl]benzo[b]thiophene Dioxalate

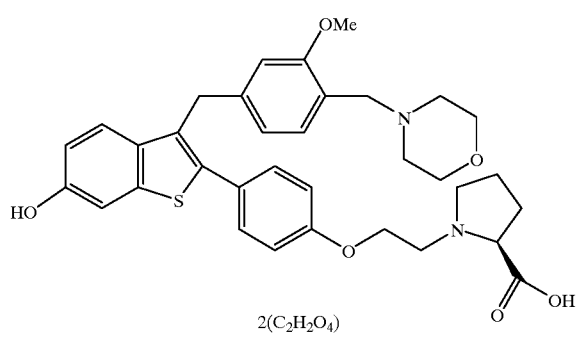

Following the procedure described in Example 2, the hydroxy acid salt was obtained from the hydroxy ester of Example 3 as a white solid in an overall 75% yield.

IR (KBr) 3400–2500 (br), 1726, 1672, 1610 $cm^{-1}$; FDMS m/e 603 ($M^++1-2[C_2H_2O_4]$); Anal. Calcd. for $C_{34}H_{38}N_2O_6S.1.7(C_2H_2O_4)$: C, 59.43; H, 5.52; N, 3.71. Found: C, 59.42; H, 5.33; N, 4.03.

EXAMPLE 5

Preparation of 2-[4-[2-[2-(S)-(tert-Butoxycarbonyl)-pyrrolidin-1-yl]ethoxy]phenyl]-6-(hydroxy)benzo[b]thiophen-3-yl 3-Methoxy-4-[(1-pyrrolidinyl)methyl]phenyl Ketone

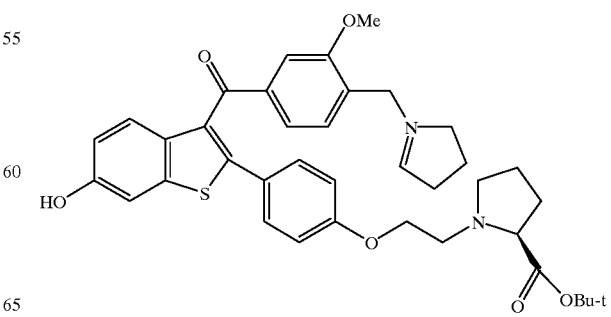

A. 6-Benzyloxy-2-[4-[2-(hydroxy)ethoxy]phenyl]-benzo[b]thiophen-3-yl 3-Methoxy-4-[(1-pyrrolidinyl)-methyl]phenyl Ketone

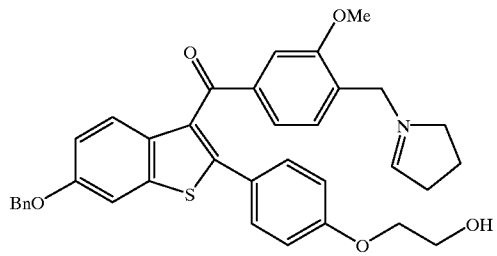

Following the procedure described in Example 1-B, the hydroxy ketone was obtained from the silyl ether of Example 1-A and 6-benzyloxy-2-(dimethylamino)benzo[b]thiophen-3-yl 3-methoxy-4-[(1-pyrrolidinyl)methyl]phenyl ketone as a foam in an overall 73% yield.

IR (neat) 3364 (br), 1651, 1605 cm$^{-1}$; FDMS m/e 593 M$^+$); Anal. Calcd. for $C_{36}H_{35}NO_5S$: C, 72.83; H, 5.94; N, 2.36. Found: C, 72.68; H, 5.89; N, 2.44.

B. 6-Benzyloxy-2-[4-[2-[2-(S)-(tert-butoxycarbonyl)-pyrrolidin-1-yl]ethoxy]phenyl]benzo[b]thiophen-3-yl 3-Methoxy-4-[(1-pyrrolidinyl)methyl]phenyl Ketone

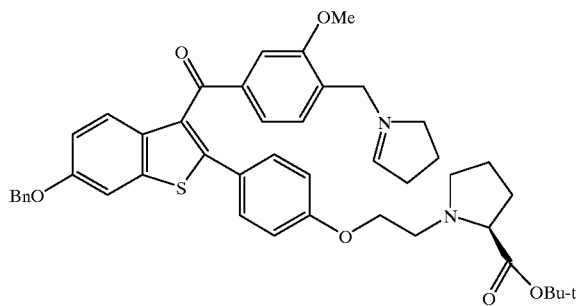

Following the procedure described in Example 1-C, the keto ester was obtained from the above hydroxy-ketone as a foam in an overall 98% yield.

IR (neat) 1732, 1651, 1605 cm$^{-1}$; FDMS m/e 747 (M$^+$+1).

C. 2-[4-[2-[2-(S)-(tert-Butoxycarbonyl)pyrrolidin-1-yl]-ethoxy]phenyl]-6-(hydroxy)benzo[b]thiophen-3-yl 3-Methoxy-4-[(1-pyrrolidinyl)methyl]phenyl Ketone Following the debenzylation procedure described in Example 1-D, the hydroxy ester was obtained from the above benzyloxy ester as a foam in an overall 54% yield.

IR (neat) 3400 (br), 1738, 1651, 1604 cm$^{-1}$; FDMS m/e 657 (M$^+$+1); Anal. Calcd. for $C_{38}H_{44}N_2O_6S$: C, 69.49; H, 6.75; N, 4.26. Found: C, 69.73; H, 6.73; N, 4.10.

The 6-benzyloxy-2-(dimethylamino)benzo[b]thiophen-3-yl 3-methoxy-4-[(1-pyrrolidinyl)methyl]phenyl ketone used in part A, above, may be obtained using a method similar to that described in Example 9-A, below, but using 3-methoxy-4-[(1-pyrrolidinyl)methyl]benzoic acid hydrochloride. The benzoic acid may be obtained in a manner similar to the following preparation.

D. Methyl 4-Bromomethyl-3-methoxybenzoate

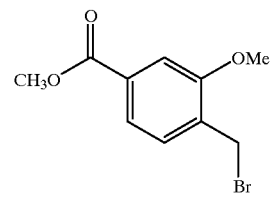

Methyl 3-methoxy-4-methylbenzoate (9.95 g; 55.2 mmol) and N-bromosuccinimide (10.81 g; 60.7 mmol) were combined in 250 mL of CCl$_4$ and heated to reflux. AIBN (0.75 g; 5.5 mmol) was added and the resultant mixture was heated at reflux for 8 h. The mixture was refrigerated, then filtered and concentrated under reduced pressure. The residue was triturated with hexanes and filtered to give the bromo ester as white needles (11.7 g; 82% yield).

$^1$H NMR (CDCl$_3$) δ7.63 (d, J=7.6 Hz, 1H), 7.58 (s, 1H) 7.41 (d, J=7.9 Hz, 1H), 4.56 (s, 2H), 3.98 (s, 3H), 3.94 (s, 3H); FDMS 528 (M+).

E. Methyl 3-Methoxy-4-[(1-pyrrolidinyl)methyl]benzoate

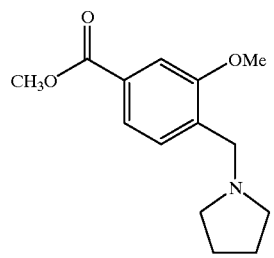

Methyl 4-bromomethyl-3-methoxybenzoate (1.0 g; 3.9 mmol) (Part D) was dissolved in THF (10 mL) and pyrrolidine (1.3 mL; 15.4 mmol) was added at room temperature. The mixture was stirred overnight at room temperature, then poured into 50 mL of water. Extraction was carried out with EtOAc (4×25 mL). The combined organics were washed with brine and dried by passage through sodium sulfate. The title compound was isolated (0.92 g; 96% yield) by flash chromatography on silica gel eluting with EtOAc (100–95%)/Et$_3$N(0–5%).

$^1$H NMR (CDCl$_3$) δ7.62 (d, J=7.8 Hz, 1H), 7.51 (s, 1H) 7.43 (d, J=7.7 Hz, 1H), 3.90 (s, 3H), 3.87 (s, 3H), 3.69 (s, 2H), 2.57 (m, 4H), 1.79 (m, 4H)

F. 3-Methoxy-4-[(1-pyrrolidinyl)methyl]benzoic Acid Hydrochloride

The ester conveniently is hydrolyzed using 1.1 to 1.5 equivalents of 1 N LiOH in THF/MeOH (3:1) for 3 h at 50° C. or overnight at room temperature, followed by careful acidification at room temperature with hydrochloric acid (5 N to 12 N) and evaporation. The benzoic acid hydrochloride from one such preparation was characterized as follows.

$^1$H NMR (DMSO-d$_6$) δ1.89–1.94 (br s, 4H), 3.01–3.05 (br s, 2H), 3.26–3.34 (br s, 2H), 3.88 (s, 3H), 4.32 (s, 2H), 7.53 (s, 1H), 7.54 (d, J=7.7 Hz, 1H), 7.70 (d, J=7.7 Hz, 1H) FDMS m/e 235 (M+).

EXAMPLE 6

Preparation of 6-Hydroxy-2-[4-[2-[2-(S)-(carboxy) pyrrolidin-1-yl]ethoxy]phenyl]benzo[b]thiophen-3-yl 3-Methoxy-4-[(1-pyrrolidinyl)methyl]phenyl Ketone Dioxalate

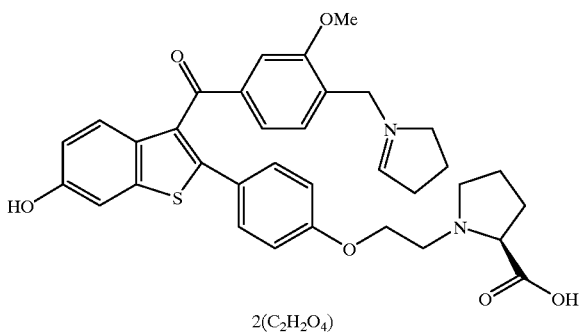

Following the procedure described in Example 2, the keto acid was obtained from the keto ester of Example 5 as a yellowish solid in an overall 71% yield.

IR (KBr) 3400–2500 (br), 1726, 1640, 1606 cm$^{-1}$; FDMS m/e 601 (M$^+$+1−2[C$_2$H$_2$O$_4$]); Anal. Calcd. for C$_{34}$H$_{36}$N$_2$O$_6$S.1.7(C$_2$H$_2$O$_4$): C, 59.59; H, 5.27; N, 3.72. Found: C, 59.55; H, 5.48; N, 3.71.

EXAMPLE 7

Preparation of 2-[4-[2-[2-(S)-(tert-Butoxycarbonyl)-pyrrolidin-1-yl]ethyl]phenyl]-6-(hydroxy)benzo[b]thiophen-3-yl 3-Methoxy-4-[(1-pyrrolidinyl)methyl]phenyl Ketone

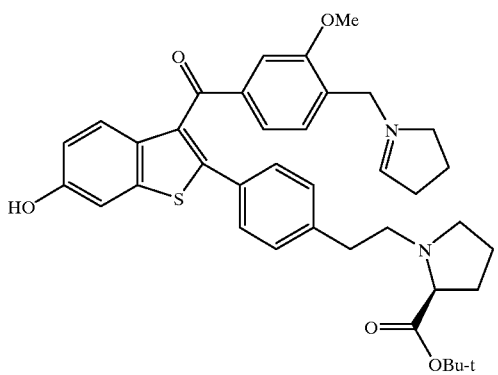

A. 6-Benzyloxy-2-[4-[2-[2-(S)-(tert-butoxycarbonyl)-pyrrolidin-1-yl]ethyl]phenyl]benzo[b]thiophen-3-yl 3-Methoxy-4-[(1-pyrrolidinyl)methyl]phenyl Ketone

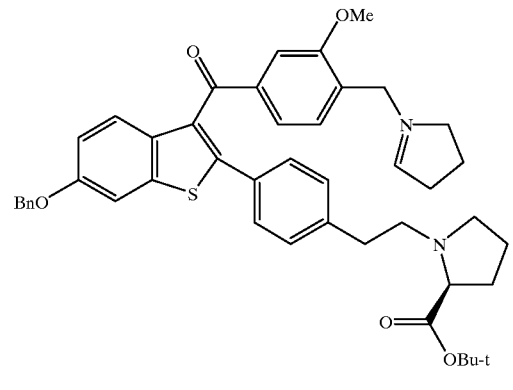

Following the procedure described in Example 1-C, the keto ester was obtained from 6-benzyloxy-2-[4-(2-hydroxyethyl)phenyl]benzo[b]thiophen-3-yl 3-methoxy-4-[(1-pyrrolidinyl)methyl]phenyl ketone. Column chromatography on silica [gradient 25–0% toluene in 75–100% EtOAc, then 0.5–2% Et$_3$N in EtOAc] gave 814 mg (83%) of the product as a yellow oil.

IR (neat) 3021, 1733, 1646, 1601 cm$^{-1}$; FDMS m/e 730 (M$^+$); Anal. Calcd. for C$_{45}$H$_{50}$N$_2$O$_5$S: C, 73.94; H, 6.89; N, 3.83. Found: C, 74.11; H, 6.71; N, 3.65.

B. 2-[4-[2-[2-(S)-(tert-Butoxycarbonyl)pyrrolidin-1-yl]-ethyl]phenyl]6-(hydroxy)benzo[b]thiophen-3-yl 3-Methoxy-4-[(1-pyrrolidinyl)methyl]phenyl Ketone Following the debenzylation procedure described in Example 1-D, the hydroxy ester was obtained from the above benzyloxy ester. Column chromatography on silica [gradient 0–10% EtOH/Et$_3$N (2/1) 10–30% THF in hexanes] gave 429 mg (63%) of the product as a yellow solid.

IR (neat) 3450 (br), 2971, 1728, 1653, 1597 cm$^{-1}$; FDMS m/e 641 (M$^+$+1).

The 6-benzyloxy-2-[4-(2-hydroxyethyl)phenyl]-benzo[b]thiophen-3-yl 3-methoxy-4-[(1-pyrrolidinyl)methyl]-phenyl ketone of Part A was obtained using a procedure similar to the following.

C. 1-Bromo-4-[2-(triisopropylsilyloxy)ethyl]benzene

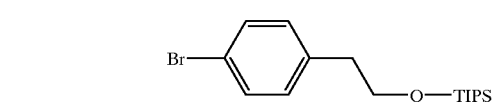

Triisopropylsilyl trifluoromethanesulfonate (35.1 mL, 130 mmol) was added to a stirred solution of 4-bromophenethyl alcohol (20.2 g, 100 mmol) and anhydrous triethylamine (27.8 mL, 200 mmol) in anhydrous CH$_2$Cl$_2$ (200 mL) at room temperature under nitrogen atmosphere. The resultant mixture was stirred for 3 h. After dilution with EtOAc (200 mL), the mixture was washed with a mixed aqeous solution of saturated NaHCO$_3$ (50 mL) and brine (50 mL), dried over MgSO$_4$, filtered, concentrated, and chromatographed on silica (gradient 0–10% EtOAc in hexanes) to give 33.5 g (94%) of the silyl ether as an oil.

IR (CHCl$_3$) 2944, 1489 cm$^{-1}$; $^1$H NMR (CDCl$_3$) δ1.03 (br s, 3H), 1.39 (br s, 18H), 2.81 (t, J=6.8 Hz, 2H), 3.86 (t, J=6.8 Hz, 2H), 7.11 (d, J=8.2 Hz, 2H), 7.40 (d, J=8.2 Hz, 2H); FDMS m/e 356 (M$^+$, $^{79}$Br) and 358 (M$^+$, $^{81}$Br)

D. 6-Benzyloxy-2-[4-(2-hydroxyethyl)phenyl]-benzo[b]thiophen-3-yl 3-Methoxy-4-[(1-pyrrolidinyl)methyl]-phenyl Ketone

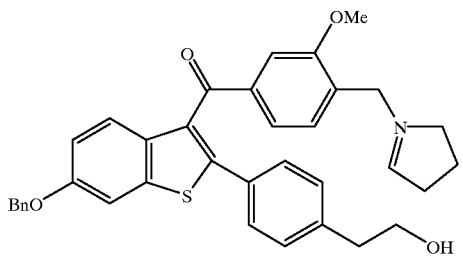

The above silyl ether (571 mg, 1.60 mmol) was added to a stirred suspension of magnesium ribbons (36.4 mg, 1.50 mmol) in anhydrous THF (2 mL) under argon atmosphere, followed by the addition of a small iodine crystal. The mixture was heated in an oil bath at 60–65° C. for 2 h to form a homogeneous Grignard solution. The Grignard solution was cooled to room temperature before it was added to a stirred solution of 6-benzyloxy-2-(dimethylamino)-benzo[b]thiophen-3-yl 3-methoxy-4-[(1-pyrrolidinyl)-methyl]phenyl ketone (500 mg, 1.00 mmol) in anhydrous THF (4 mL) at 0° C. under argon atmosphere. The resultant mixture was stirred at 0° C. for 1.5 h, then quenched with saturated aqueous NH$_4$Cl (5 mL). After extraction with EtOAc (25 mL×2), the combined organic layers were dried over MgSO$_4$, filtered, and concentrated to give a gummy residue (597 mg).

The residue was dissolved in anhydrous THF (5 mL) and treated with tetrabutylammonium fluoride (1.20 mL, 1 M in THF) at room temperature under nitrogen atmosphere. After stirring for 1.5 h, the mixture was concentrated under vacuum and chromatographed on silica [gradient 0–30% EtOH/Et$_3$N (2/1) in THF/hexanes (1/1)] to give 395 mg (68%) of the alcohol as a foam.

IR (CHCl$_3$) 2960, 1646, 1601 cm$^{-1}$; $^1$H NMR (CDCl$_3$) δ1.80 (br s, 4H), 2.54 (br s, 4H), 2.75 (t, J=6.2 Hz, 2H), 3.59 (s, 2H), 3.74 (t, J=6.2 Hz, 2H), 3.79 (s, 3H), 5.18 (s, 2H), 7.05 (d, J=8.1 Hz, 1H), 7.09–7.50 (m, 13H), 7.74 (d, J=8.9 Hz, 1H); FDMS m/e 578 (M+1); Anal. Calcd for C$_{36}$H$_{35}$NO$_4$S: C, 74.84; H, 6.11; N, 2.42. Found: C, 75.02; H, 6.34; N, 2.50.

EXAMPLE 8

Preparation of 6-Hydroxy-2-[4-[2-[2-(S)-(carboxy)-pyrrolidin-1-yl]ethyl]phenyl]benzo[b]thiophen-3-yl 3-Methoxy-4-[(1-pyrrolidinyl)methyl]phenyl Ketone Dioxalate

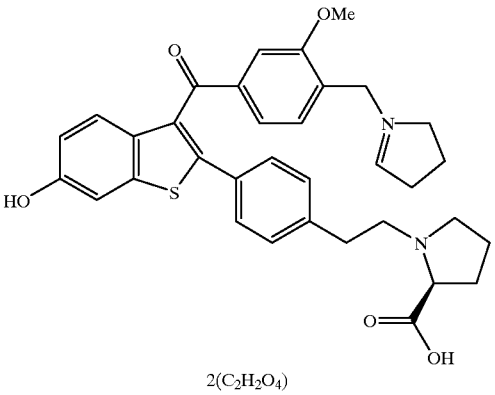

Following the procedure described in Example 2, the hydroxy acid salt was obtained from the hydroxy-ester of Example 7 as a yellow solid in an overall 91% yield.

IR (KBr) 3400 (br), 3300–2220 (br), 2973, 1726, 1642, 1609 cm$^{-1}$; FDMS m/e 585 (M$^+$+1−2[C$_2$H$_2$O$_4$]); Anal. Calcd. for C$_{34}$H$_{36}$N$_2$O$_5$So1.5(C$_2$H$_2$O$_4$): C, 61.74; H, 5.46; N, 3.86. Found: C, 61.93; H, 5.54; N, 3.82.

EXAMPLE 9

Preparation of 3-[4-[[2-(S)-(tert-Butoxycarbonyl)-pyrrolidin-1-yl]methyl]-3-(methyl)benzyl]-6-hydroxy-2-[4-[2-(1-pyrrolidinyl)ethoxy]phenyl]benzo[b]thiophene

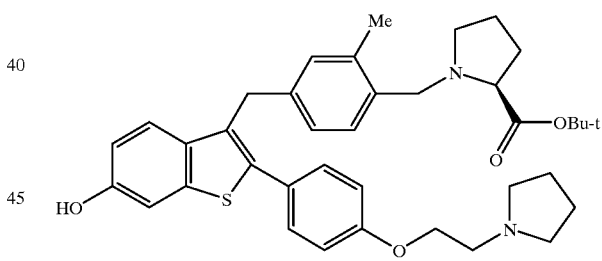

A. 6-Benzyloxy-2-(dimethylamino)benzo[b]thiophen-3-yl 4-Bromo-3-(methyl)phenyl Ketone

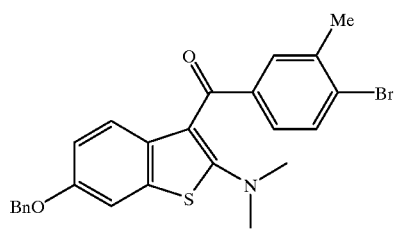

Oxalyl chloride (15.8 mL, 181 mmol) was added to a stirred suspension of 4-bromo-3-methylbenzoic acid (6.00 g, 27.9 mmol) in anhydrous CH$_2$Cl$_2$ (40 mL), followed by the addition of 2 drops of DMF. The suspension was stirred at room temperature under nitrogen atmosphere for 6 h, then it was concentrated to dryness.

To the crude benzoyl chloride suspended in anhydrous chlorobenzene (50 mL) was added 6-benzyloxy-2-(dimethyl-amino)benzo[b]thiophene (6.33 g, 22.3 mmol). The resultant mixture was heated in an oil bath at 110° C. for 2 h. At room temperature, the mixture was diluted with EtOAc (160 mL) before it was cautiously treated with saturated NaHCO$_3$ (50 mL). The organic layer was dried over MgSO$_4$, filtered, concentrated, and chromatographed on silica [gradient 0–5% EtOAc in toluene] to give 7.49 g (70%) of the amino ketone as a foam.

IR (neat) 3450, 1623, 1598 cm$^{-1}$; FDMS m/e 479 (M$^+$, $^{79}$Br) and 481 (M+, $^{81}$Br); Anal. Calcd. for C$_{25}$H$_{22}$BrNO$_2$S: C, 62.50; H, 4.62; N, 2.92. Found: C, 62.77; H, 4.59; N, 2.87.

B. 6-Benzyloxy-2-[4-[(1-pyrrolidinyl)ethoxy] phenyl]-benzo[b]thiophen-3-yl 4-Bromo-3-(methyl) phenyl Ketone

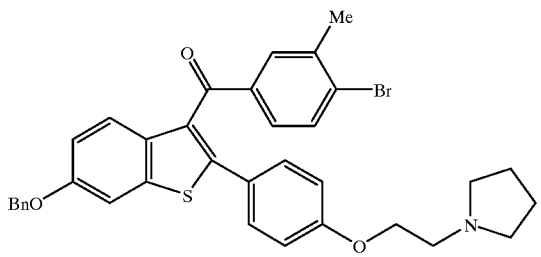

1-[2-(4-Bromophenoxy)ethyl]pyrrolidine (3.87 g, 14.3 mmol) was added to a stirred suspension of magnesium ribbons (307 mg, 12.6 mmol) in anhydrous THF (6 mL) under an argon atmosphere, followed by the addition of a small iodine chip. The resultant mixture was heated in an oil bath at 60–65° C. for 1 h to form a homogeneous Grignard solution. The Grignard solution was cooled to room temperature and diluted with anhydrous THF (10 mL) before it was added to a stirred solution of the above amino ketone (4.05 g, 8.42 mmol) in anhydrous THF (15 mL) at 0° C. under an argon atmosphere. The resultant mixture was stirred at 0° C. for 2 h, then quenched with saturated aqueous NH$_4$Cl (20 mL). After extraction with EtOAc (70 mL×2), the combined organic layers were dried over MgSO$_4$, filtered, concentrated and chromatographed on silica [gradient 0–5% Et$_3$N 50–45% hexanes in toluene] to give 5.28 g (100%) of the ketone as a yellow oil.

IR (neat) 2953, 1646, 1607 cm$^{-1}$; FDMS m/e 625 (M$^+$, $^{79}$Br) and 627 (M+, $^{81}$Br).

C. 6-Benzyloxy-2-[4-[(1-pyrrolidinyl)ethoxy] phenyl]-benzo[b]thiophen-3-yl 4-(Methoxycarbonyl)-3-(methyl)phenyl Ketone

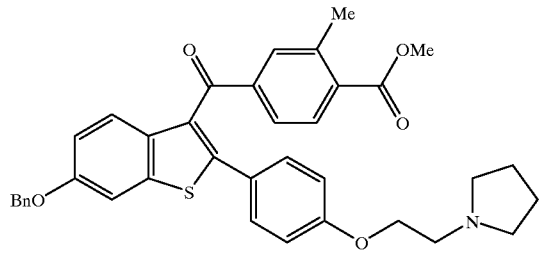

To a stirred solution of the above ketone (5.10 g, 8.14 mmol) in 25 mL anhydrous DMF were sequentially added Pd(OAc)$_2$ solid (190 mg, 0.846 mmol), 1,3-bis (diphenylphosphino)propane solid (349 mg,0.846 mmol), 12.5 mL Et$_3$N, and 12.5 mL MeOH. The reaction was purged with CO (g) and kept under a balloon CO (g) atmosphere while heating the resulting mixture at 70° C. for 8 h. The mixture was allowed to cool to room temperature, then it was diluted with 100 ml H$_2$O and 200 ml EtOAc. The aqueous layer was extracted with EtOAc (2×100 mL), then the combined organics were dried over MgSO4, filtered, concentrated, and chromatographed [gradient 0–5% EtOH/ Et$_3$N (2/1) 5–25% THF in hexanes] to give 3.26 g (64%) of the keto ester as a yellow oil.

IR (neat) 2945 (br), 1724, 1647, 1606 cm$^{-1}$; FDMS m/e 606 (M$^+$+1).

D. 6-Benzyloxy-3-[4-(hydroxymethyl)-3-(methyl) benzyl]-2-[4-[2-(1-pyrrolidinyl)ethoxy]phenyl]benzo [b]thiophene.

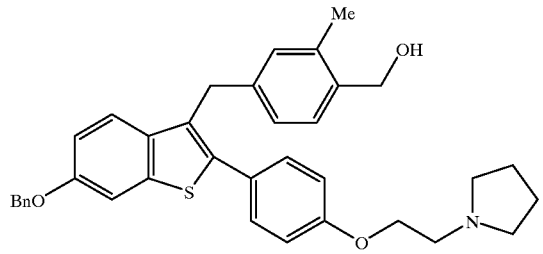

Following the procedure described in Example 3-A, the alcohol was obtained from the above keto ester. Column chromatography on silica [gradient 0–5% Et$_3$N 50–70% EtOAc in hexanes, then 10% Et$_3$N/EtOH (2/1) 70% EtOAc in hexanes] gave 2.29 g (75%) of the product as an off-white foam.

IR (neat) 3470 (br), 1607 cm$^{-1}$; FDMS m/e 564 (M$^+$+1); Anal. Calcd. for C$_{36}$H$_{37}$NO$_3$S: C, 76.70; H, 6.62; N, 2.48. Found: C, 76.58; H, 6.45; N, 2.46.

E. 6-Benzyloxy-3-[4-[[2-(S)-(tert-butoxycarbonyl)-pyrrolidin-1-yl]methyl]-3-(methyl)benzyl]-2-[4-[2-(1-pyrrolidinyl)ethoxy]phenyl]benzo[b]thiophene

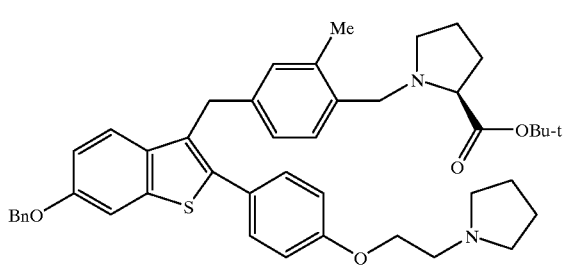

Anhydrous triethylamine (0.378 mL, 2.72 mmol) and methanesulfonyl chloride (0.105 mL, 1.36 mmol) were sequentially added to a stirred solution of the above alcohol (0.510 g, 0.905 mmol) in anhydrous dichloromethane (5 mL) at 0° C. under nitrogen atmosphere. The mixture was stirred for 1 h at 0° C. before it was treated with (L)-proline t-butyl ester (0.370 mL, 2.26 mmol). The cold bath was removed and the resultant mixture was stirred for an additional 4 h. After dilution with $CH_2Cl_2$/EtOAc (20 mL/30 mL), the mixture was washed with saturated $NaHCO_3$ (20 mL), dried, filtered, concentrated, and chromatographed on silica [gradient 0–5% $Et_3N$ in EtOAc] to give a 395 mg (61%) of the benzyloxy ester as a foam.

IR (neat) 1727, 1608 $cm^{-1}$; FDMS m/e 717 ($M^++1$); Anal. Calcd. for $C_{45}H_{52}N_2O_4S$: C, 75.38; H, 7.31; N, 3.91. Found: C, 75.09; H, 7.16; N, 3.74.

F. 3-[4-[[2-(S)-(tert-Butoxycarbonyl)pyrrolidin-1-yl]-methyl]-3-(methyl)benzyl]-6-hydroxy-2-[4-[2-(1-pyrrolidinyl)ethoxy]phenyl]benzo[b]thiophene

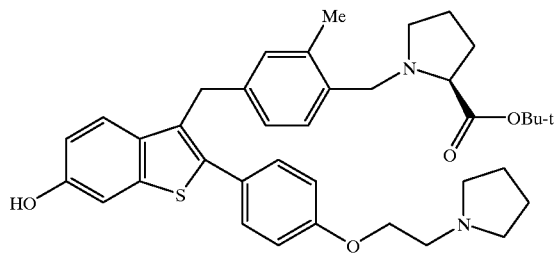

Following the debenzylation procedure described in Example 1-D, the hydroxy ester was obtained from the above benzyloxy ester as a foam in a 64% yield.

IR (neat) 3150 (br), 1727, 1608 $cm^{-1}$; FDMS m/e 627 ($M^++1$).

The 6-benzyloxy-2-(dimethylamino)benzo[b]thiophene was prepared in a manner similar to the following.

G. α-(4-Benzyloxyphenyl)-α-hydroxy-N,N-dimethyl-thioacetamide

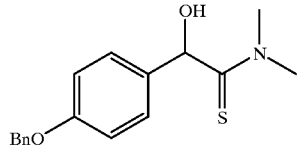

To a solution of distilled diisopropylamine (22.9 mL, 175 mmol) in 400 mL of anhydrous THF at −78° C. was added 1.6 M n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated $NH_4Cl$ solution. The mixture was extracted with EtOAc (3×1 L), and the combined organic layers were dried over $MgSO_4$ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for $C_{17}H_{19}NO_2S$: C, 67.75; H, 6.35; N, 4.65. Found: C, 67.61; H, 6.37; N, 4.57.

H. 6-Benzyloxy-2-(dimethylamino)benzo[b]thiophene

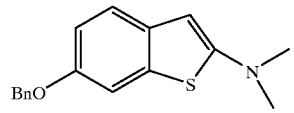

To a solution of thioacetamide (Part G) (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous $NaHCO_3$ solution, followed by addition of 3 mL of $H_2O$, and stirred vigorously. The layers were separated and the organic layer was dried over $MgSO_4$ and concentrated under reduced pressure. The residue was then purified by flash chromatography (silica gel, 10% $Et_2O$/hexanes) to afford 327 mg (1.15 mmol, 70%) of a white solid.

mp 78–81° C.; FDMS 283 (M+); Anal. Calcd for $C_{17}H_{17}NOS$: C, 72.05; H, 6.05; N, 4.94. Found: C, 72.22; H, 6.15; N, 4.89.

EXAMPLE 10

Preparation of 6-Hydroxy-3-[4-[[2-(S)-(hydroxycarbonyl)-pyrrolidin-1-yl]methyl]-3-(methyl)benzyl]-2-[4-[2-(1-pyrrolidinyl)ethoxy]phenyl]benzo[b]thiophene Dioxalate

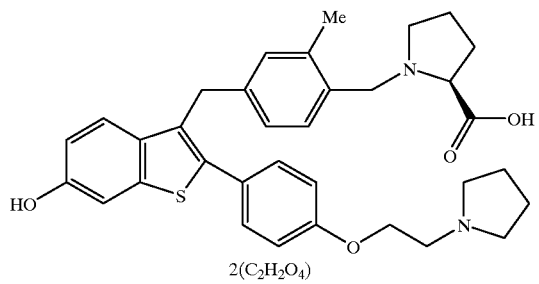

Following the procedure described in Example 2, the hydroxy acid salt was obtained from the hydroxy ester of Example 9 as a white solid in an overall 78% yield.

IR (KBr) 3400–2500 (br), 1715, 1673, 1609 cm$^{-1}$; FDMS m/e 571 (M$^{+}$+1−2[C$_2$H$_2$O$_4$]); Anal. Calcd. for C$_{34}$H$_{38}$N$_2$O$_4$S.1.7(C$_2$H$_2$O$_4$): C,62.06; H, 5.77; N, 3.87. Found: C,62.18; H, 5.66; N, 3.94.

EXAMPLE 11

Preparation of 2-[4-[2-(4-Carboxymethylimidazol-1-yl)-ethoxy]phenyl]-3-[4-[2-(1-pyrrolidinyl)ethoxy]benzyl]-benzo[b]thiophene Dihydrochloride

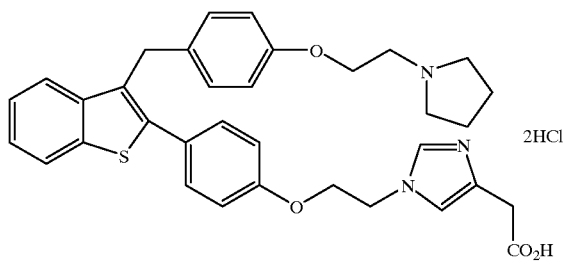

A. 2-[4-[2-(tert-Butyldiphenylsilyloxy)ethoxy]phenyl]-3-[4-[2-(1-pyrrolidinyl)ethoxy]benzyl]benzo[b]thiophene

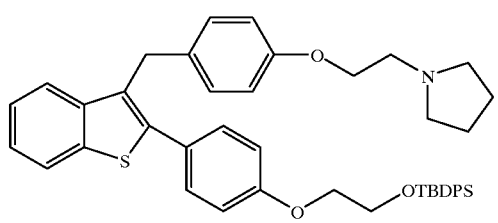

A mixture of 2.00 g (4.66 mmol) of 2-(4-hydroxyphenyl)-3-[4-[2-(1-pyrrolidinyl)ethoxy]benzyl]benzo[b]thiophene, 1.86 g (5.12 mmol) of 1-bromo-2-(tert-butyldiphenylsilyloxy)ethane, and 1.93 g (14.0 mmol) of K$_2$CO$_3$ in 50 mL DMF was heated to 50° C. for 22 h. The reaction was poured into 250 mL of H$_2$O and the mixture extracted with EtOAc (3×100 mL). The combined organic extracts were washed with H$_2$O (2×100 mL), dried over K$_2$CO$_3$, filtered and concentrated in vacuo to give 4.21 g of an oily solid. Purification by flash chromatography (SiO$_2$; 0.1% then 0.2% then 0.5% MeOH in CHCl$_3$ sat'd with NH$_4$OH) afforded 2.76 g (3.88 mmol; 83%) of the title compound as an oil.

FDMS 711 (M+); Anal. calcd for C$_{45}$H$_{49}$NO$_3$S: C, 75.91; H, 6.94; N, 1.97. Found: C, 76.05; H, 6.98; N, 2.12.

B. 2-[4-[2-(Hydroxy)ethoxy]phenyl]-3-[4-[2-(1-pyrrolidinyl)ethoxy]benzyl]benzo[b]thiophene

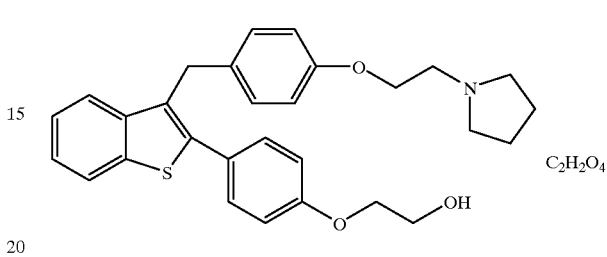

By essentially following the conditions described in Example 1, Part B, the title compound was prepared as a solid from the above silyl ether in 93% yield following flash chromatography (SiO$_2$; 2% then 4% MeOH in CHCl$_3$ sat'd with NH$_4$OH).

FDMS 473 (M+); Anal. calcd for C$_{29}$H$_{31}$NO$_3$S.C$_2$H$_2$O$_4$: C, 66.06; H, 5.91; N, 2.49. Found: C, 65.88; H, 5.68; N, 2.58.

C. 2-[4-[2-(4-Methoxycarbonylmethylimidazol-1-yl)-ethoxy]phenyl]-3-[4-[2-(1-pyrrolidinyl)ethoxy]benzyl]-benzo[b]thiophene.

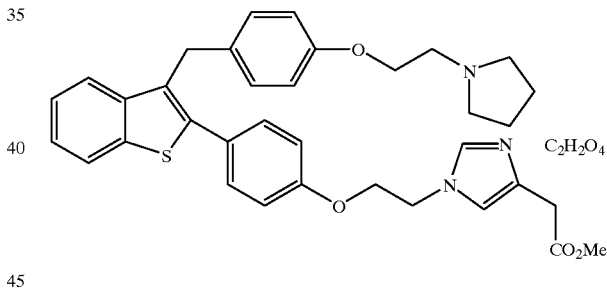

A 0° C. solution of 500 mg (1.06 mmol) of the above alcohol, 440 mg (3.18 mmol) of K$_2$CO$_3$, and 1 drop of TEA in 20 mL of CH$_2$Cl$_2$ was treated with 0.12 mL (1.6 mmol) of methanesulfonyl chloride. The reaction was stirred for 2 hrs and was washed with H$_2$O (2×20 mL). The mixture was dried over K$_2$CO$_3$, filtered, and concentrated in vacuo.

A 0° C. slurry of 100 mg (2.61 mmol) of NaH (60% by weight dispersion in mineral oil) was treated with a solution of 393 mg (2.22 mmol) of 4-imidazoleacetic acid methyl ester and the mixture stirred until gas evolution ceased. The resulting solution was added via cannula to the mesylate that was formed in the preceeding paragraph. The reaction was stirred at 0° C. for 1 h and at ambient temperature for 3 h. The mixture was poured into brine and the two layers separated. The aqueous layer was extracted with EtOAc (3×50 mL). The combined organic layers were washed with H$_2$O (50 mL), dried over K$_2$CO$_3$, filtered, and concentrated in vacuo to afford an oil. Purification by radial chromatography (SiO$_2$; 5% MeOH in CHCl$_3$ sat'd with NH$_4$OH) afforded 257 mg (0.43 mmol; 41%) of the free base of the title compound. A portion of the product was converted to the oxalate salt using a procedure similar to that described in Example 1-D, but using MeOH as the solvent.

FDMS 596 (M+1); Anal. calcd for $C_{35}H_{37}N_3O_4S \cdot C_2H_2O_4 \cdot 1.2 H_2O$: C, 62.82; H, 5.90; N, 5.94. Found: C, 62.44; H, 5.58; N, 6.02.

D. 2-[4-[2-(4-Carboxymethylimidazol-1-yl)ethoxy]phenyl]-3-[4-[2-(1-pyrrolidinyl)ethoxy]benzyl]benzo[b]thiophene Dihydrochloride A portion of the above ester (200 mg; 0.34 mmol) was taken up in 5 mL of 1 N aq HCl and the solution heated to 50° C. for 5 h. The solution was lyophilized to afford 199 mg (95%) of the title compound.

FDMS 583 (M+1); Anal. calcd for $C_{34}H_{35}N_3O_4S \cdot 2HCl \cdot 0.6 H_2O$: C, 61.37; H, 5.79; N, 6.31. Found: C, 61.01; H, 6.15; N, 6.46.

The 2-(4-hydroxyphenyl)-3-[4-[2-(1-pyrrolidinyl)ethoxy]benzyl]benzo[b]thiophene starting material may be obtained by either of the methods described below.

E. 2-(4-Methoxyphenyl)benzo[b]thiophene

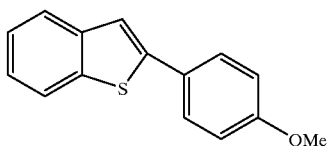

The title compound was prepared in 91% yield from benzo[b]thiophene-2-boronic acid and 4-bromoanisole by using a coupling procedure similar to that described below in Example 14-A.

mp 188–191° C.; $^1$H NMR (DMSO-$d_6$) δ7.94 (d, J=8.0 Hz, 1H), 7.81 (d, J=7.0 Hz, 1H), 7.73 (m, 2H) . 7.71 (s, 1H), 7.35 (m, 2H), 7.05 (d, J=8.0 Hz, 2H), 3.82 (s, 3H); FDMS 240 (M$^+$; 100); Anal. Calcd for $C_{21}H_{23}NO_2S$: C, 71.36; H, 6.56; N, 3.86. Found: C, 71.46; H, 6.60; N, 3.86.

F. 2-(4-Methoxyphenyl)benzo[b]thiophen-3-yl 4-[2-(1-Pyrrolidinyl)ethoxy]phenyl Ketone

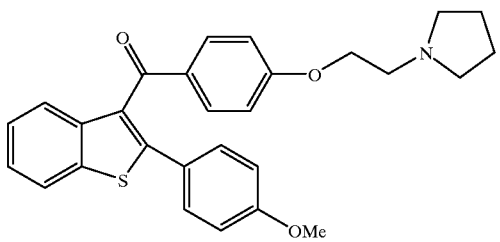

By converting 4-[2-(1-pyrrolidinyl)ethoxy]benzoic acid hydrochloride into the corresponding benzoyl chloride hydrochloride using thionyl chloride and catalytic DMF in refluxing dichloromethane to form the benzoyl choride, followed by acylation using AlCl$_3$ in 1,2-dichloroethane at 0° C., the title compound was prepared from 2-(4-methoxyphenyl)benzo[b]thiophene in 59% yield as an oil following radial chromatography (SiO$_2$; gradient of 2–5% MeOH in CH$_2$Cl$_2$).

G. 2-(4-Hydroxyphenyl)benzo[b]thiophen-3-yl 4-[2-(1-Pyrrolidinyl)ethoxy]phenyl Ketone

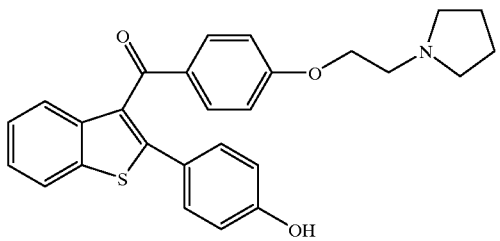

By cleaving the methyl ether of 2-(4-methoxyphenyl)-benzo[b]thiophen-3-yl 4-[2-(1-pyrrolidinyl)ethoxy]phenyl ketone using AlCl$_3$ (about 8 eq) and EtSH (about 10 eq) in dichloroethane at 0° C., the title compound was obtained in 33% yield as an oil following radial chromatography (SiO$_2$; gradient of 2–10% MeOH in CH$_2$Cl$_2$).

FDMS 443 (M$^+$; 100); Anal. Calcd For $C_{27}H_{25}NO_3S$: C, 73.11; H, 5.68; N, 3.16. Found: C, 73.11; H, 5.89; N, 3.20.

H. 2-(4-Hydroxyphenyl)-3-[4-[2-(1-pyrrolidinyl)ethoxy]-benzyl]benzo[b]thiophene

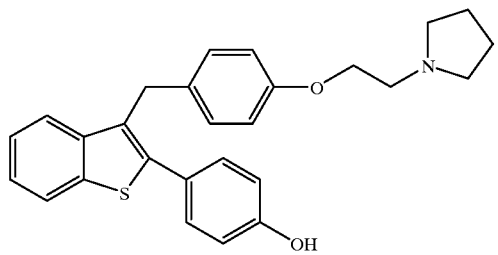

A 0° C. solution of 7.40 g (16.7 mmol) of 2-(4-hydroxyphenyl)benzo[b]thiophen-3-yl 4-[2-(1-pyrrolidinyl)ethoxy]-phenyl ketone in 500 mL of THF was treated with 67.0 mL of a solution of DIBAL-H (1 N in toluene; 67 mmol). The reaction was stirred at 0° C. for 1 h and was quenched by the careful addition of 50 mL of MeOH. Saturated aq. sodium/potassium tartrate (200 mL) and EtOAc (200 mL) were added and the reaction stirred vigourously for 1 h. The two layers were separated and the aqueous layer was extracted with EtOAc (3×200 mL). The combined organic layers were dried (K$_2$CO$_3$), filtered and concentrated in vacuo. The residue was taken up in dichloroethane (300 mL). The solution was cooled to 0° C. and was treated with 20.0 mL (125 mmol) of triethylsilane followed by 13.0 mL (168 mmol) of trifluoroacetic acid. The reaction was stirred at 0° C. for 1 h and was poured into 250 mL of sat'd aq. NaHCO$_3$. The two layers were separated and the organic layer was dried (K$_2$CO$_3$), filtered, and concentrated in vacuo to give 6.53 g of a foam. Flash chromatography (SiO$_2$; 25% THF: 5% TEA: 70% hexanes) afforded 5.45 g (12.7 mmol; 76%) of the title compound as a foam.

$^1$H NMR (DMSO-$d_6$) d 9.77 (s, 1H), 7.90 (d, J=8.8 Hz, 1H), 7.93–7.87 (m, 1H), 7.32–7.24 (m, 4H), 6.97 (d, J=8.7 Hz, 2H), 6.86–6.75 (m, 4H), 4.13 (s, 2H), 3.97 (t, J=5.8 Hz, 2H), 2.87–2.78 (m, 2H), 2.61–2.52 (m, 4H), 1.69–1.61 (m, 4H).

I. 2-(4-Methoxyphenyl)benzo[b]thiophen-3-yl 4-[2-(1-Pyrrolidinyl)ethoxy]phenyl Ketone

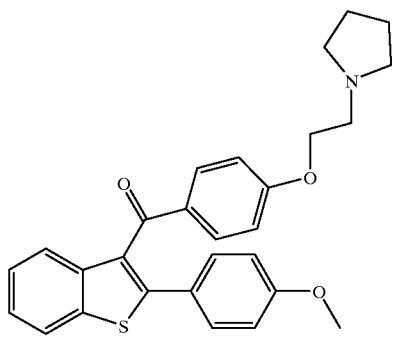

Sodium hydride (0.69 g of 60% NaH in mineral oil; 17.22 mMol) was suspended in 15 mL of dry DMF in a flame-dried, argon-filled flask. After stirring for 15 min, a solution of 4-(1-pyrrolidinyl)ethanol was added. After stirring for 15 min and gas evolution had ceased, 4-fluorophenyl 2-(4-methoxyphenyl)benzo[b]thiophen-3-yl ketone [prepared by acylation of 2-(4-methoxyphenyl)benzo[b]thiophene with 4-fluorobenzoyl chloride](5.2 g; 14.34 mmol) in 15 mL of dry DMF was added. The mixture was stirred at room temperature for 5 h, then poured into 25 mL of water. Extraction was carried out with EtOAc (4×25 mL). The combined organics were washed with brine and dried by passage through sodium sulfate. The title compound (5.12 g; 78% yield) was isolated as a colorless oil by flash chromatography on silica gel, eluting with a gradient of EtOAc (100–85%)/Et$_3$N(0–5%)/MeOH(0–10%).

[1]NMR (CDCl$_3$) δ7.85 (m, 1H), 7.76 (d, J=6.3, 2H), 7.63 (m, 1H), 7.36 (m, 4H), 6.77 (d, J=7.2, 4H), 4.22 (t, J=5.3, 2H) 3.75 (s, 3H), 3.04 (t, J=5.2, 2H), 2.83 (br s, 4H), 1.90 (br s, 4H); FDMS 457 (M).

J. 2-(4-Methoxyphenyl)-3-[4-[2-(1-pyrrolidinyl)ethoxy]-benzyl]benzo[b]thiophene

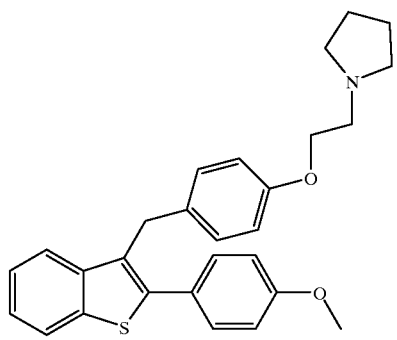

To the above ketone (Part I) (3.12 g; 11.2 mmol) in 40.0 mL of THF was added 0.42 g (11.2 mmol) of LAH at 0° C. The bath was removed and the mixture was stirred for 1 h. Hydrolysis was effected by addition of 0.42 mL of water, 0.42 mL of 5N NaOH, and 1.26 mL of water, followed by stirring for 1 h. After the mixture was filtered and washed with THF, the filtrate was concentrated; and the intermediate carbinol was dried in vacuo for 25 min. The carbinol was dissolved in methylene chloride (40.0 mL) under argon atmosphere and cooled in an ice-water bath. Triethylsilane (12.5 mL; 78.3 mmol) was added, followed by dropwise addition of 8.6 mL (112.0 mmol) of TFA. Upon completion of addition of TFA, the bath was removed and stirring was continued for 2 h. Saturated aqueous sodium bicarbonate (50 mL) was added, and extraction was carried out with EtOAc. The combined organics were washed with brine and dried by passage through sodium sulfate. The title compound (4.45 g; 90% yield) was isolated as a colorless oil by flash chromatography on silica gel, eluting with a gradient of EtOAc (100–95%)/Et$_3$N(0–5%).

[1]NMR (CDCl$_3$) δ7.87 (m, 1H), 7.77 (d, J=6.4, 2H), 7.65 (m, 1H), 7.34 (m, 4H), 6.78 (d, J=7.4, 4H), 4.20 (s, 2H), 4.15 (t, J=5.3, 2H), 3.73 (s, 3H), 3.14 (t, J=5.4, 2H), 2.91 (br s, 4H), 1.90 (br s, 4H); FDMS 444 (M+1).

K. 2-(4-Hydroxyphenyl)-3-[4-[2-(1-pyrrolidinyl) ethoxy]-benzyl]benzo[b]thiophene

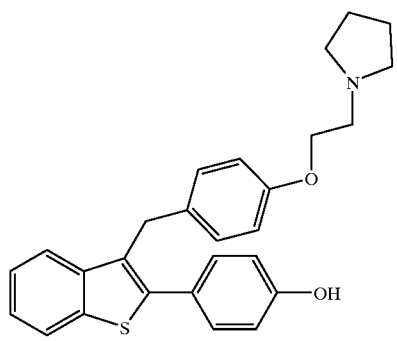

The above methyl ether (4.5 g; 10.1 mmol) (Part J) was dissolved in 45 mL of dichloroethane under an argon atmosphere and cooled in an ice-water bath. To this was added ethanethiol (6.0 mL; 81.1 mmol) and 5.41 g (40.6 mmol) of aluminum chloride, and the mixture was stirred in the cold bath for 1 h. Saturated NaHCO$_3$ was added, and stirring was continued while warming to room temperature for 1 h. The title compound (0.23 g; 74% yield) was isolated by filtration and washed with water.

[1]NMR (CDCl$_3$) δ7.83 (m, 1H), 7.47 (m, 1H), 7.29 (m, 2H), 6.98 (d, J=8.5, 2H), 6.83 (m, 4H), 6.69 (d, J=8.6, 2H), 4.15 (m, 4H), 3.05 (m, 2), 2.85 (br s, 4H), 1.91 (br s, 4H); FDMS 430 (M+1).

EXAMPLE 12

Preparation of 3-[4-[2-(1-Pyrrolidinyl)ethoxy] benzyl]-2-[4-[2-(2-ethoxy-2-oxoethylamino)ethoxy] phenyl]-benzo[b]thiophene

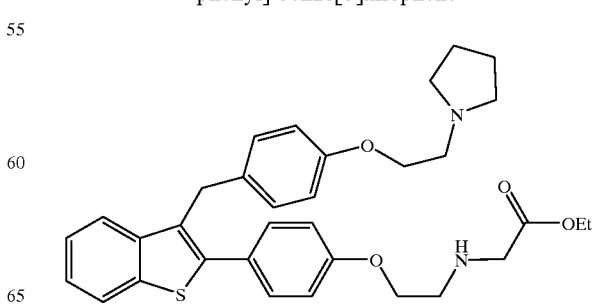

A. 2-[4-[2-(t-Butyloxycarbonylamino)ethoxy]phenyl]-3-[4-[2-(1-pyrrolidinyl)ethoxy]benzyl]benzo[b]thiophene Oxalate

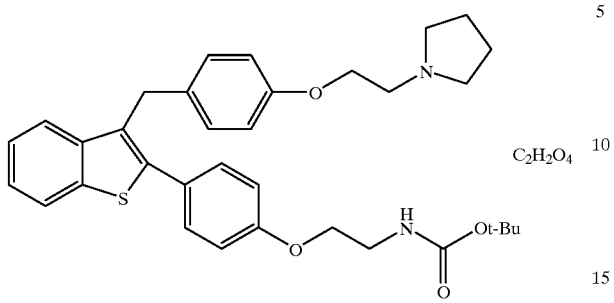

A mixture of 2.0 g (4.66 mmol) of 2-(4-hydroxyphenyl)-3-[4-[2-(1-pyrrolidinyl)ethoxy]benzyl]benzo[b]thiophene (Example 11-D), 1.47 g (5.60 mmol) of triphenylphosphine, and 0.90 g (5.60 mmol) of N-t-Boc-aminoethanol in 20 mL of THF was cooled to 5° C. and was treated with 0.88 mL (5.60 mmol) of diethyl azodicarboxylate. The cooling bath was removed and the reaction stirred at ambient temperature for 23 hours. The mixture was diluted with 20 mL of saturated NaCl solution and the layers were separated. The organic layer was dried over $K_2CO_3$, filtered and concentrated in vacuo to afford 5.47 g of an oil. Purification by flash chromatography (SiO$_2$; 2% then 5% MeOH in CHCl$_3$ saturated with NH$_4$OH) afforded 1.43 g (2.50 mmol; 54%) of the free base of the title compound as a foam. The product was converted to the oxalate salt according to the method described in Example 11-C.

FDMS 487 (M+1); Anal. Calcd for $C_{34}H_{38}N_2O_{10}S$: C, 61.25; H, 5.75; N, 4.20. Found: C, 60.98; H, 5.66; N, 4.00.

B. 2-[4-(2-Aminoethoxy)phenyl]-3-[4-[2-(1-pyrrolidinyl)-ethoxy]benzyl]benzo[b]thiophene Dihydrochloride

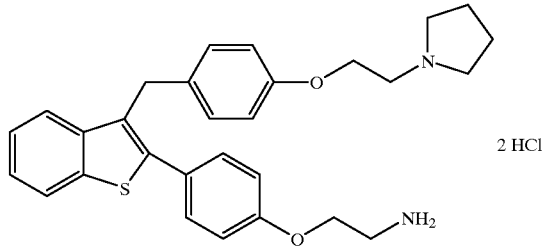

A solution of 1.20 g (2.10 mmol) of the above urethane (Part B) in 5.0 mL of anisole was treated with 10.0 mL of TFA. The reaction was stirred overnight and was concentrated in vacuo. The residue was partitioned between 50 mL of 1 N aq HCl and 50 mL of hexanes. The aqueous layer was separated, washed with hexanes (2×50 mL) and EtOAc (2×50 mL), and lyopholized to afford 964 mg (1.77 mmol; 84%) of the title compound.

FDMS 487 (M+1); Anal. Calcd for $C_{29}H_{32}N_2O_2S$. 2 HCl: C, 63.84; H, 6.28; N, 5.13. Found: C, 64.14; H, 6.33; N, 5.11.

C. 3-[4-[2-(1-Pyrrolidin-1-yl)ethoxy]benzyl]-2-[4-[2-(2-ethoxy-2-oxoethylamino)ethoxy]phenyl]benzo[b]thiophene

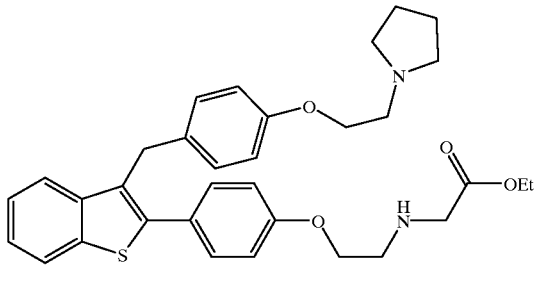

3-[4-[2-(1-Pyrrolidin-1-yl)ethoxy]benzyl]-2-[4-(2-aminoethoxy)phenyl]benzo[b]thiophene (146 mg) was dissolved in dichloromethane (7.0 mL), treated with ethyl glyoxalate (65 µL, 50% in toluene) and sodium triacetoxyborohydride (84 mg) sequentially and allowed to stir at ambient temperature for 4 h. The reaction mixture was concentrated and fractionated by column chromatography with Et$_3$N:MeOH:EtOAc (5:10:85) followed by NH$_4$OH:MeOH:EtOAc (5:10:85) afforded the product (106 mg).

FDMS m/e: found 559(M+H$^+$); $^1$H NMR(CDCl$_3$): δ7.83 (d, 1H), 7.51(d, 1H), 7.42(d, 2H), 7.28(m, 2H), 7.05(d, 2H), 6.95(d, 2H), 6.83(d, 2H), 4.21 (m, 4H), 4.11 (m, 4H), 3.52(s, 2H), 3.06(t, 2H), 2.94(t, 2H), 2.69(m, 4H), 1.84 (m, 4H), 1.30(t, 3H).

EXAMPLE 13

Preparation of 2-[4-[2-(2-Carboxymethylamino)ethoxy]phenyl]-3-[4-[2-(1-pyrrolidinyl)ethoxy]benzyl]benzo[b]thiophene

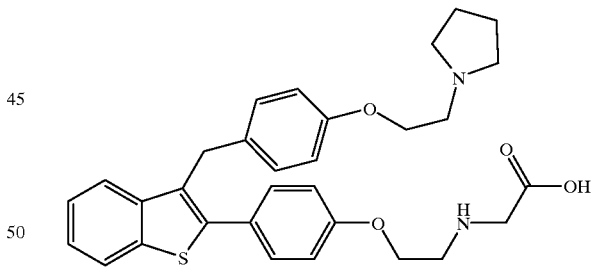

3-[4-[2-(1-Pyrrolidinyl)ethoxy]benzyl]-2-[4-[2-(2-ethoxy-2-oxoethylamino)ethoxy]phenyl]benzo[b]thiophene (64 mg) was dissolved in THF:MeOH:H$_2$O (3:1:1, 3 mL), treated with LiOH-H$_2$O (6 mg) and allowed to stir at ambient temperature for 17 h. The reaction mixture was concentrated under reduced pressure. Chromatography with NH$_4$OH:MeOH: -EtOAc (10:20:70) afforded the title compound (50 mg).

FDMS m/e: found 531(M+H$^+$); $^1$H NMR(CDCl$_3$): δ7.72 (m, 1H), 7.44(m, 1H), 7.29(m, 4H), 6.93(d, 2H), 6.84(d, 2H), 6.70(d, 2H), 5.80(bm, 1H), 5.69 (bm, 1H), 4.10 (bm, 2H), 4.08(s, 2H), 3.53(bm, 2H), 3.24(bm, 2H), 3.01(bm, 2H), 2.83(m, 4H), 1.84(m, 4H).

EXAMPLE 14

Preparation of 2-[4-[2-(4-Methoxycarbonylbenzylamino)ethyl]-phenyl]-3-[4-[2-(1-pyrrolidinyl)ethoxy]benzyl]-benzo[b]thiophene

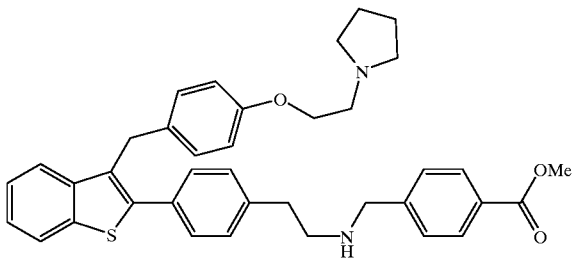

A. 2-[4-(Cyanomethyl)phenyl]benzo[b]thiophene

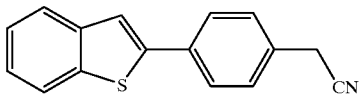

Benzo[b]thiophen-2-yl boronic acid (1.25 g) and 4-bromobenzyl nitrile (1.51 g) were dissolved in THF (25 mL), treated with a solution of sodium carbonate in water (2.0 M, 7.0 mL) and tetrakis(triphenylphosphine)palladium (0.25 g) and allowed to stir at reflux in the dark for 15 h. The cooled reaction mixture was diluted with water (100 mL) and extracted with dichloromethane (100 mL×3). The combined organic layers were dried with sodium sulfate and concentrated. The off-white solid was triturated with ethyl acetate and the product was collected as a white precipitate by centrifugation (1.5 g).

$^1$H NMR (CDCl$_3$): δ7.77 (d, 1H), 7.68 (d, 1H), 7.31 (d, 2H) 7.30 (d, 2H), 7.28(m, 2H), 7.20(s, 1H), 3.75(s, 2H).

B. 2-[4-(Cyanomethyl)phenyl]benzo[b]thiophen-3-yl 4-(2-(1-Pyrrolidin-1-yl)ethoxy]phenyl Ketone

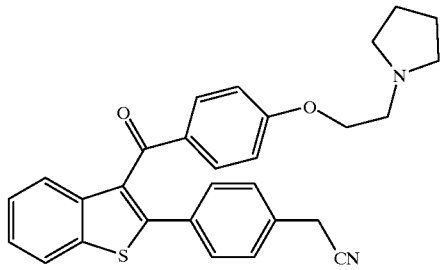

To a solution of 2-[4-(cyanomethyl)phenyl]benzo[b]thiophene (265 mg) and 4-[2-(1-pyrrolidinyl)ethoxy]benzoyl chloride (385 mg) in dichloromethane (20 mL) at 0° C. in the dark was added TiCl$_4$ (1.3 mL, neat) slowly under argon. The resulting mixture was stirred at 0° C. to ambient temperature for 5.5 h before it was transferred carefully to a stirring solution of saturated aqueous NaHCO$_3$ (100 mL). After stirring for 30 min, the mixture was extracted with CH$_2$Cl$_2$ (3×100 mL). The combined organic layers were dried (Na$_2$SO$_4$) and concentrated under reduced pressure. Chromatography with Et$_3$N:EtOAc (5%) afforded the product (230 mg).

$^1$H NMR(CDCl$_3$): δ7.97(d, 1H), 7.86(d, 2H), 7.75(d, 1H), 7.56(d, 2H), 7.47(m, 2H), 7.33(d, 2H), 6.87(d, 2H), 4.21(t, 2H), 3.80(s, 2H), 3.00(t, 2H), 2.72(m, 4H), 1.91(m, 4H).

C. 2-[4-(Cyanomethyl)phenyl]-3-[4-[2-(1-pyrrolidinyl)-ethoxy]benzyl]benzo[b]thiophene

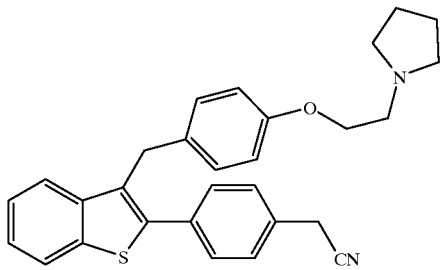

2-[4-(Cyanomethyl)phenyl]benzo[b]thiophen-3-yl 4-[2-(1-pyrrolidinyl)ethoxy]phenyl ketone (158 mg) in THF (5.0 mL) was treated with lithium aluminum hydride (13 mg) at 0° C. for 2 h, and then quenched with water (0.5 mL) and sodium hydroxide (5.0 M, 0.5 mL). Stirring was continued for 10 min. The reaction mixture was diluted with brine (50 mL) and extracted with dichloromethane (3×50 mL). The combined organic layers were dried with sodium sulfate and concentrated in vacuo to give a yellow foam-like material. This material was dissolved in dichloromethane (5 mL), treated with triethylsilane (0.3 mL) and trifluroacetic acid (0.2 mL) at 0° C. for 1.5 h, and concentrated under reduced pressure. The residue was extracted with dichloromethane (50 mL×3) from saturated aqueous sodium bicarbonate (50 mL). The combined organic layers were dried with sodium sulfate and concentrated. Chromatography with Et$_3$N:EtOAc (0–5%) afforded the product (106 mg).

$^1$H NMR(CDCl$_3$): δ7.93(d, 1H), 7.60(d, 1H), 7.58(d, 2H), 7.42(d, 2H), 7.34(m, 2H), 7.09(d, 2H), 6.86(d, 2H), 4.24(s, 2H), 4.15(t, 2H), 3.83(s, 2H), 2.97(t, 2H), 2.67(m, 4H), 1.85(m, 4H).

D. 2-[4-(2-Aminoethyl)phenyl]-3-[4-[2-(1-pyrrolidinyl)-ethoxy]benzyl]benzo[b]thiophene

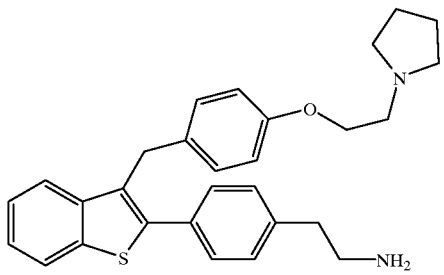

2-[4-(Cyanomethyl)phenyl]-3-[4-[2-(1-pyrrolidinyl)-ethoxy]benzyl]benzo[b]thiophene (1.39 g) was dissolved in ethanol and warmed to 55° C. before it was treated with Raney nickel (1 mL slurry in water) followed by addition of hydrazine monohydrate (1.5 mL). The resulting mixture was allowed to stir at 55° C. for 30 min or until the evolution of gas had stopped. The cooled reaction mixture was filtered through diatomaceous earth, rinsed with methanol and dichloromethane. The filtrate was diluted with saturated sodium bicarbonate (50 mL) and extracted with dichloromethane (50 mL×3). The combined organic layers were dried with sodium sulfate and concentrated. Chromatography with NH₄OH:MeOH:EtOAc (5:10:85) afforded the product (1.30 g).

¹H NMR(CDCl₃): δ7.89(d, 1H), 7.54(d, 1H), 7.49(d, 2H), 7.30(m, 4H), 7.09(d, 2H), 6.86(d, 2H), 4.27(s, 2H), 4.11(t, 2H), 3.04(t, 2H), 2.92(t, 2H), 2.82(m, 2H), 2.65(m, 4H), 1.84(m, 4H).

E. 2-[4-[2-(4-Methoxycarbonylbenzylamino)ethyl] phenyl]-3-[4-[2-(1-pyrrolidinyl) ethoxy]benzyl] benzo[b]thiophene 3-[4-[2-(1-Pyrrolidinyl)ethoxy]benzyl]-2-[4-(2-amino-ethyl)phenyl]benzo[b]thiophene (165 mg) was dissolved in dichloromethane (4.0 mL), treated with 4-methoxycarbonylbenzaldehyde (59 mg) and sodium triacetoxyborohydride (80 mg) sequentially and allowed to stir at ambient temperature for 4 h. The reaction mixture was concentrated and fractionated by column chromatography with Et₃N:MeOH:EtOAc (5:10:85) afforded the product (74 mg) along with a bis(4-methoxycarbonylbenzyl) side product (68 mg).

FDMS m/e: found 605 (M+H⁺); ¹H NMR(CDCl₃): δ8.12 (d, 2H), 7.95(d, 1H), 7.62(d, 1H), 7.55(d, 2H), 7.48(d, 2H), 7.40(m, 4H), 7.16(d, 2H), 6.92(d, 2H), 4.35(s, 2H), 4.21(t, 2H), 4.01(s, 3H), 3.97(s, 2H), 3.02(m, 6H), 2.82 (m, 4H), 1.93(m, 4H).

EXAMPLE 15

Preparation of 2-[4-[2-(4-Carboxybenzylamino) ethyl]phenyl]-3-[4-[2-(1-pyrrolidinyl)ethoxy]benzyl] benzo[b]thiophene

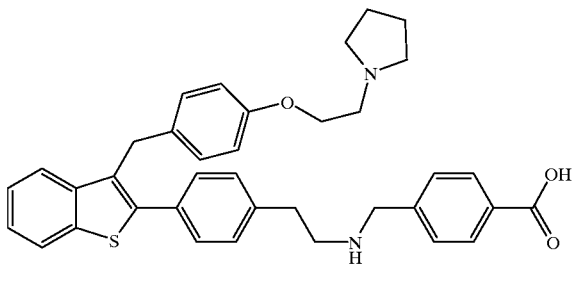

3-[4-[2-(1-Pyrrolidinyl)ethoxy]benzyl]-2-[4-[2-(4-methoxycarbonylbenzylamino)ethyl]phenyl]benzo[b] thiophene (47 mg) was dissolved in THF:MeOH:H₂O (3:1:1, 3 mL), treated with LiOH-H₂O (5 mg) in one portion and allowed to stir at ambient temperature for 62 h. The reaction mixture was concentrated under reduced pressure. Chromatography with NH₄OH:MeOH:EtOAc (5:10:85) afforded the title compound (32 mg).

FDMS m/e: found 591(M+H⁺); ¹H NMR(CDCl₃): δ8.02 (d, 2H), 7.96(d, 1H), 7.62(d, 1H), 7.52(d, 2H), 7.40(m, 4H), 7.28(d, 2H), 7.16(d, 2H), 6.85(d, 2H), 4.37(m, 2H), 4.30(s, 2H), 4.01(s, 2H), 3.30(m, 2H), 3.20(m, 2H), 3.03 (m, 4H), 2.03(m, 4H).

EXAMPLE 16

Preparation of 2-[4-[2-(2-Ethoxy-2-oxoethylamino) ethyl]-phenyl]-3-[4-[2-(1-pyrrolidinyl)ethoxy] benzyl]-benzo[b]thiophene

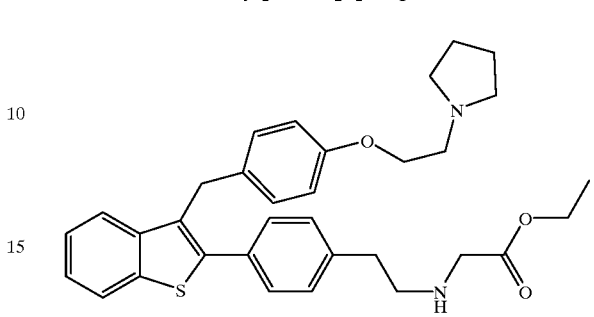

3-[4-[2-(1-Pyrrolidin-1-yl)ethoxy]benzyl]-2-[4-(2-aminoethyl)phenyl]benzo[b]thiophene (140 mg) was dissolved in dichloromethane (7.0 mL), treated with a solution of ethyl glyoxalate in toluene (50%, 63 μL) and sodium triacetoxy-borohydride (84 mg) sequentially and allowed to stir at ambient temperature for 4 h. The reaction mixture was concentrated and fractionated by column chromatography with Et₃N:MeOH:EtOAc (5:5:90) afforded the product (52 mg).

¹H NMR (CDCl₃): δ7.85 (d, 1H), 7.50 (d, 1H), 7.46 (d, 2H), 7.28 (m, 4H), 7.06(d, 2H), 6.83(d, 2H), 4.24(s, 2H), 4.19(q, 2H), 4.10 (t, 2H), 3.45(s, 2H), 2.93(m, 4H), 2.67(m, 4H), 1.83(m, 4H), 1.28 (t, 3H).

EXAMPLE 17

Preparation of 2-[4-[2-(Carboxymethylamino)ethyl] phenyl]-3-[4-[2-(pyrrolidin-1-yl)ethoxy]benzyl] benzo[b]thiophene

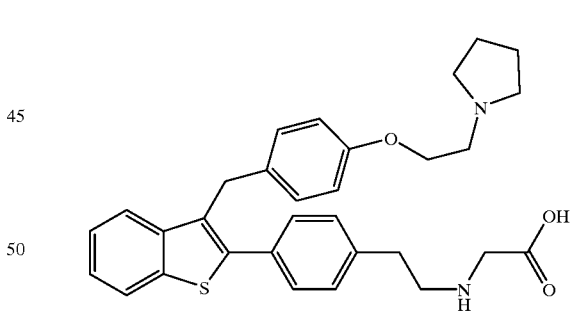

3-[4-[2-(1-Pyrrolidin-1-yl)ethoxy]benzyl]-2-[4-(2-aminoethyl)phenyl]benzo[b]thiophene (210 mg) was dissolved in THF:MeOH (5:1, 6.0 mL), treated with glyoxalic acid (50 mg) and sodium triacetoxy-borohydride (150 mg) sequentially and allowed to stir at ambient temperature for 5 h. The reaction mixture was concentrated and fractionated by column chromatography with NH₄OH:MeOH:EtOAc (5:10:85) afforded the product (97 mg).

FDMS m/e: found 515 (M+H⁺); ¹H NMR(CDCl₃): δ7.80 (d, 1H), 7.57(d, 1H), 7.42(d, 2H), 7.40(m, 2H), 7.24(d, 2H), 7.02(d, 2H), 6.80(d, 2H), 4.20(m, 4H), 3.64 (bs, 2H), 3.21(m, 2H), 3.08(m, 4H), 2.93(m, 4H), 1.95(m, 4H).

EXAMPLE 18

Preparation of (S)-2-[4-[3-(3-Amino-1,4-dioxo-4-hydroxybutylamino)propyloxy]phenyl]-3-[4-[2-(1-pyrrolidinyl)-ethoxy]benzyl]benzo[b]thiophene.

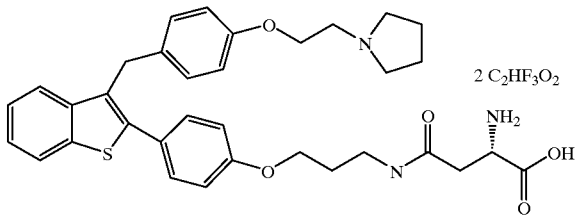

2 C$_2$HF$_3$O$_2$

A. 2-[4-[3-(1-Phthalimidyl)propyloxy]phenyl]-3-[4-[2-(1-pyrrolidinyl)ethoxy]benzyl]benzo[b]thiophene

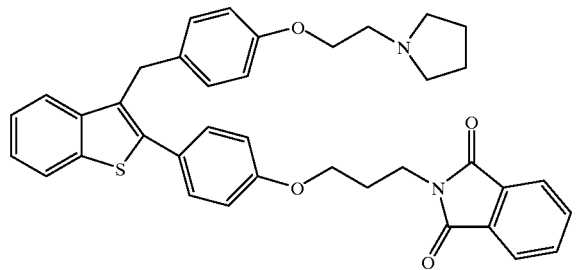

To 2-(4-hydroxyphenyl)-3-[4-[2-(1-pyrrolidinyl)-ethoxy]benzyl]benzo[b]thiophene (15 mg, 0.116 mmol) in THF (0.5 mL) was added potassium hexamethyldisilazane (KHMDS) (0.5 M in toluene, 0.255 mL, 0.128 mmol) and the mixture stirred under N$_2$ for 30 minutes. N-(3-Bromopropyl)-phthalimide (310 mg, 0.116 mmol) in THF (0.5 mL) and a catalytic amount of Bu$_4$NI was added to the phenoxide solution and heated at reflux for 5 h. After cooling to room temperature, the mixture was diluted 25 fold with EtOAc, the organics washed with saturated NaHCO$_3$ (aq) and H$_2$O and concentrated under reduced pressure. Material was purified by flash chromatography (SiO$_2$, 10% MeOH in CHCl$_3$); yielding the titled compound in 71% yield.

$^1$H NMR (CDCl$_3$) δ7.83–7.88 (m, 3H), 7.71–7.75 (m, 2H), 7.50 (d, J=5.7 Hz, 1H), 7.38 (d, J=8.5 Hz, 2H), 7.29–7.34 (m, 2H), 7.06 (d, J=8.2 Hz, 2H), 6.79–6.88 (m, 4H), 4.34 (t, J=4.1 Hz, 2H), 4.21 (s, 2H), 4.08 (t, J=3.7 Hz, 2H), 3.94 (t, J=3.0 Hz, 2H), 3.24 (t, J=4.0 Hz, 2H), 3.12 (s, 4H), 2.03–2.24 (m, 2H), 2.02 (s, 4H); FDMS 616.3.

B. 2-[4-(3-Aminopropyloxy])phenyl]-3-[4-[2-(1-pyrrolidinyl)ethoxy]benzyl]benzo[b]thiophene

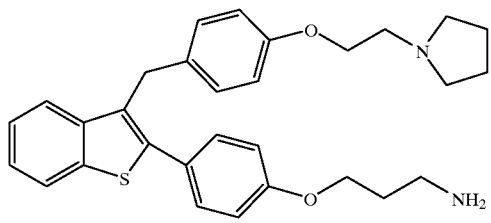

To the above named phthalimide (0.338 g, 0.548 mmol) in EtOH (3 mL), was added H$_2$NNH$_2$.H$_2$O (85%, 0.172 mL, 5.48 mmol) and the mixture heated at 65° C. for 1 h. After cooling to room temperature, the mixture was concentrated under reduced pressure and the resulting residue taken up in EtOAc. The organics were washed with saturated NaHCO$_3$ (aq) and H$_2$O and reconcentrated. Material was purified by flash chromatography (SiO$_2$, 10% MeOH in CHCl$_3$ with 1% Et$_3$N v/v added) to afford the titled compound in 73% yield.

$^1$H NMR (CDCl$_3$) δ7.82 (d, J=8.4 Hz, 1H), 7.51 (d, J=6.3 Hz, 1H), 7.41 (d, J=8.6 Hz, 2H), 7.28 (m, 2H), 7.03 (d, J=8.4 Hz, 2H), 6.91 (d, J=8.6 Hz, 2H), 6.81 (d, J=8.4 Hz, 2H), 4.19 (s, 2H), 4.10 (m, 4H), 3.02 (s, 2H), 2.90 (t, J=5.9 Hz, 2H), 2.65 (s, 4H), 2.04 (m, 2H), 1.82 (s, 4H); FDMS 487 (M+1).

C. (S)-2-[4-[3-(4-t-Butyloxy-3-t-butyloxycarbonylamino-1,4-dioxobutylamino)propyloxy]phenyl]-3-[4-[2-(1-pyrrolidinyl)ethoxy]benzyl]benzo[b]thiophene

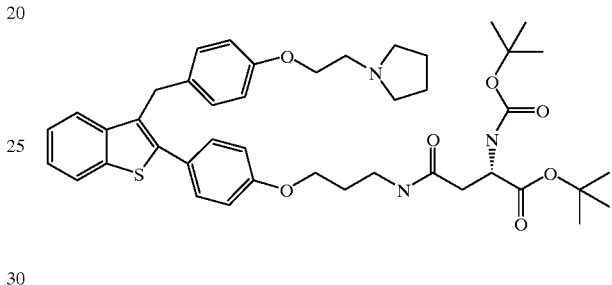

To the above amine (31 mg, 0.064 mmol) was added N-Boc-L-Asp-α-O-t-Bu (18 mg, 0.064 mmol), 1-(3-dimethylaminopropyl)-3-ethylcarbodiimide hydrochloride (25 mg, 0.128 mmol), a catalytic amount of 4-dimethylaminopyridine, and CH$_2$Cl$_2$ (0.5 mL). The mixture was stirred at room temperature for 45 minutes and then diluted 50 fold with EtOAc. The organics were washed with saturated NaHCO$_3$ (aq), H$_2$O, brine, and concentrated under reduced pressure. The material was purified by flash chromatography (SiO$_2$, 10% MeOH in CHCl$_3$) to afford the titled compound in 94% yield.

$^1$H NMR (CDCl$_3$) δ7.86 (d, J=6.2 Hz, 1H), 7.54 (d, J=6.5 Hz, 1H), 7.44 (d, J=8.6 Hz, 2H), 7.33 (m, 2H), 7.07 (d, J=8.4 Hz, 2H), 6.95 (d, J=8.6 Hz, 2H), 6.84 (d, J=8.5 Hz, 2H), 4.42 (m, 1H), 4.22 (m, 4H), 4.08 (t, J=5.8 Hz, 2H), 3.49 (q, J=4.4, 12.5 Hz, 2H), 3.08 (t, J=4.6 Hz, 2H), 2.73–2.88 (m 6H), 2.05 (m, 2H), 1.94 (s, 4H), 1.49 (s, 9H), 1.46 (s, 9H); FDMS 758.9 (M+1).

D. (S)-2-[4-[3-(3-Amino-1,4-dioxo-4-hydroxybutylamino)-propyloxy]phenyl]-3-[4-[2-(1-pyrrolidinyl)ethoxy]benzyl]-benzo[b]thiophene To the above carbamate (38 mg, 0.050 mmol) was added TFA (2 mL) and the solution allowed to stand for 1 h at room temperature. After concentrating under reduced pressure, the resulting residue was triturated with Et$_2$O and the off white solid collected and dried under vacuum to afford the titled compound in 96% yield.

$^1$H NMR (CD$_3$OD) δ7.83 (d, J=7.2 Hz, 1H), 7.48 (d, J=6.7 Hz, 1H), 7.42 (d, J=8.7 Hz, 2H), 7.26 (m, 2H), 7.07 (d, J=8.6 Hz, 2H), 6.98 (d, J=8.7 Hz, 2H), 6.89 (d, J=8.6 Hz, 2H), 4.25 (m, 5H), 4.06 (t, J=6.0 Hz, 2H), 3.61 (bs, 2H), 3.46 (t, J=7.0 Hz, 2H), 3.39 (t, J=6.9 Hz, 2H), 3.19 (bs, 2H), 2.88 (t, J=6.3 Hz, 2H), 2.01 (m, 6H); FAB MS 602.4 (M+1).

EXAMPLE 19

Preparation of (S)-2-[4-(3-Amino-1,4-dioxo-4-hydroxybutylamino)phenyl]-6-hydroxy-3-[3-methoxy-4-[(1-pyrrolidinyl)-methyl]benzyl]benzo[b]thiophene Dihydrochloride

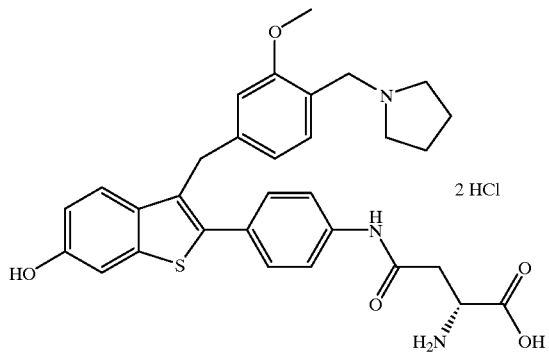

A. (S)-2-[4-(3-t-Butoxycarbonylamino-1,4-dioxo-4-t-butoxy-butylamino)phenyl]-6-benzyloxy-3-[3-methoxy-4-[(1-pyrrolidinyl)methyl]benzyl]benzo[b]thiophene

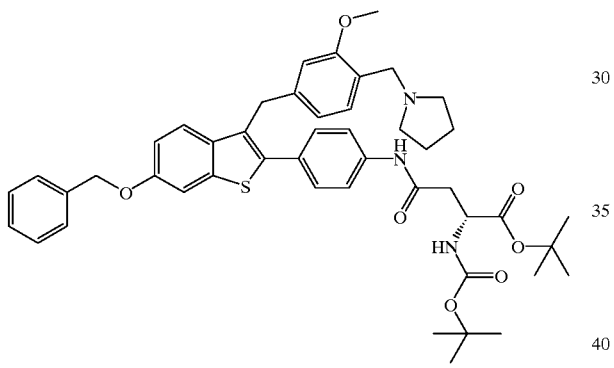

The aniline (54 mg, 0.101 mmol) [described below in part D], N-tert-butyloxycarbonyl-L-aspartic acid α-tert-butyl ester (29 mg, 0.101 mmol, 1.0 eq.), 1-(3-dimethylaminopropyl)-3-ethylcarbodiimide hydrochloride (39 mg 0.202 mmol, 2.0 eq.) and a catalytic amount of 4-dimethylamino-pyridine were placed in a pear-shaped flask then just enough dry dichloromethane (about 1 mL) was added to allow for stirring. After 18 h, the reaction mixture is diluted 50-fold with ethyl acetate then partitioned with saturated aqueous sodium bicarbonate solution (50 mL). The layers were separated then the ethyl acetate layer washed with water (25 mL), then brine (25 mL). The crude solid was purified by flash chromatography (silica, 5% methanol/chloroform) to give 77 mg (95%) of the desired product as a pale yellow foam.

FDMS (methanol): m/z=806; Anal. calcd for $C_{47}H_{55}N_3O_7S \cdot 3/2H_2O$: C, 67.76; H, 6.90; N, 5.04. Found: C, 67.74; H, 6.94; N, 5.24.

B. (S)-2-[4-(3-Amino-1,4-dioxo-4-hydroxybutylamino)-phenyl]-6-hydroxy-3-[3-methoxy-4-[(1-pyrrolidinyl)methyl]-benzyl]benzo[b]thiophene Dihydrochloride To a solution of the compound of part A above (121 mg, 0.150 mmol) in THF (1 mL) was added an aqueous solution of ammonium formate (0.2 mL of 25% w/v) and 5% Pd on carbon (121 mg, 1.0 wt. eq.). The reaction mixture was stirred vigorously at ambient temperature until the starting material had been consumed as indicated by tlc (9:1:0.1 $CHCl_3$:MeOH:TEA), then the reaction mixture was filtered through a pad of diatomaceous earth with THF (10 mL). The solvents were removed under reduced pressure and the crude residue treated with neat TFA (1 mL) at ambient temperature for 1 h. The solvent was removed under reduced pressure then the residue purified by preparative HPLC over a (VYDAC-$C_{18}$) $C_{18}$-reversed phase column, eluting over 2.5 h with a gradient of 98:2 to 50:50 (0.1% aqueous HCl):acetonitrile to afford the title compound as its dihydrochloride.

FDMS (MeOH) m/z=561.

The starting material aniline for step A above was prepared by procedures similar to the following:

C. 6-Benzyloxy-2-[4-[bis(trimethylsilyl)amino]phenyl]-benzo[b]thiophen-3-yl 3-Methoxy-4-[(1-pyrrolidinyl)methyl]-phenyl Ketone

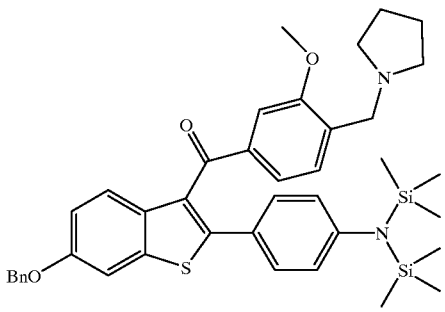

Magnesium turnings (0.25 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromo-N,N-bis(trimethylylsilyl)aniline (3.36 g) while stirring at ambient temperature. The reaction mixture was warmed to a gentle reflux for 1.5 h or until magnesium turnings were completely consumed to give a 0.5 M solution of the Grignard reagent. This freshly prepared Grignard solution (15 mL) was added slowly to a stirring solution of 6-benzyloxy-2-(dimethylamino)-benzo[b]thiophen-3-yl 3-methoxy-4-[(1-pyrrolidinyl)methyl]-phenyl ketone (see Examples 1 and 5, 2.48 g, 5.0 mmol) in THF (15.0 mL) at 0° C. under argon. The mixture was stirred at 0° C. for 3 h before quenched with saturated aqueous $NH_4Cl$ solution (50 mL) and extracted with $CH_2Cl_2$ (50 mL×3). The combined organic layers were dried with sodium sulfate and concentrated under reduced pressure. Chromatography with EtOAc-hexane (0–100% gradient elution) afforded the title compound (0.73 g).

FDMS m/e: found 693(M+); $^1$H NMR(CDCl$_3$): δ7.74(d, 1H), 7.55–7.35(m, 7H), 7.28(d, 2H), 7.22(d, 1H), 7.20(d, 1H), 7.10(d, 1H) 6.68(d, 2H), 5.17(s, 2H), 3.76(s, 3H), 3.55(s, 2H), 2.51(m, 4H), 1.78(m, 4H), 0.00(s, 18H).

D. 6-Benzyloxy-3-[3-methoxy-4-[(1-pyrrolidinyl)methyl]-benzyl]-2-(4-aminophenyl)benzo[b]thiophene

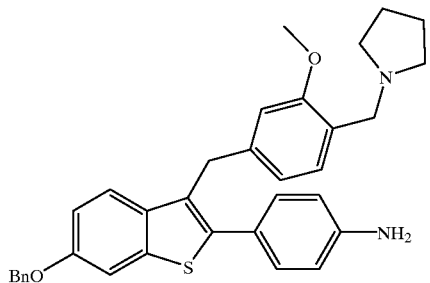

6-Benzyloxy-2-[4-[bis(trimethylsilyl)amino]phenyl]-benzo[b]thiophen-3-yl 3-methoxy-4-[(1-pyrrolidinyl)methyl]-phenyl ketone (0.73 g) was dissolved in THF (10 mL), cooled to 0° C. in an ice bath before treated with lithium aluminum hydride (110 mg) at 0° C. for 1 h, then quenched with water (1 mL) and sodium hydroxide (1.0 M, 1 mL). Stirring continued for 30 min. The reaction mixture was diluted with brine(30 mL) and extracted with dichloromethane (20 mL×3). The combined organic layers were dried with sodium sulfate and concentrated in vacuo to give the crude alcohol. This material was dissolved in dichloromethane (15 mL), treated with triethylsilane (1.5 mL) and trifluroacetic acid (1.5 mL) sequentially, allowed to stir at ambient temperature for 1.5 h, and concentrated under reduced pressure. The residue was extracted with dichloromethane (20 mL×3) from saturated aqueous sodium bicarbonate (30 mL). The combined organic layers were dried with sodium sulfate and concentrated. Chromatography with Et$_3$N:MeOH:EtOAc (5:5:90) afforded the title compound as a yellow foam (0.53 g).

FDMS m/e: found 535(M+H$^+$); $^1$H NMR(CDCl$_3$): δ7.60–7.45(m, 7H) 7.30 (d, 2H), 6.98 (d, 1H), 6.70 (m, 4H) 5.13 (s, 2H), 4.21 (s, 2H), 3.78(s, 2H), 3.70(s, 3H), 3.62(s, 2H), 2.56((m, 4H), 1.78(m, 4H).

EXAMPLE 20
Preparation of (S)-2-[5-(4-Amino-1,5-dioxo-5-hydroxypentylamino)phenyl]-6-hydroxy-3-[3-methoxy-4-[(1-pyrrolidinyl)-methyl]benzyl]benzo[b]thiophene Dihydrochloride

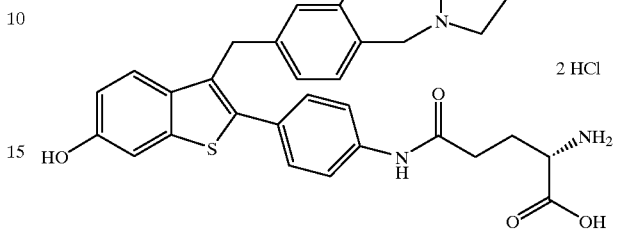

A. (S)-2-[4-(4-t-Butoxycarbonylamino-1,5-dioxo-5-t-butoxypentylamino)phenyl]-6-benzyloxy-3-[3-methoxy-4-[(1-pyrrolidinyl)methyl]benzyl]benzo[b]thiophene

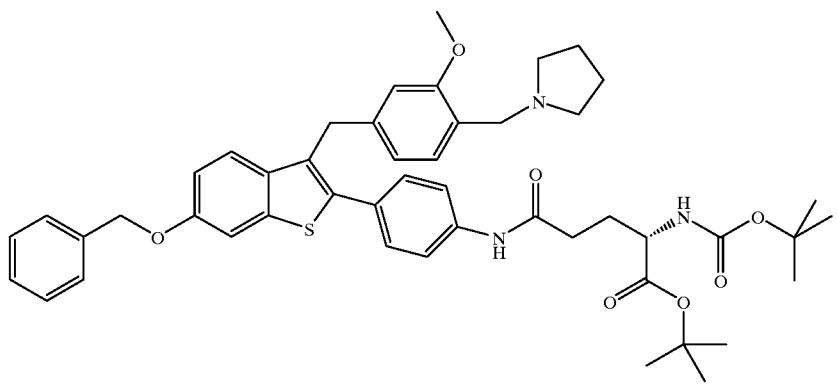

To a solution of the aniline (Example 19, Part D, 56 mg, 0.105 mmol) in CH$_2$Cl$_2$ (1 mL) was added N-Boc-L-glutamic acid α-t-butyl ester (31 mg, 0.105 mmol), 1-(3-dimethylaminopropyl)-3-ethylcarbodiimide hydrochloride (40 mg, 0.210 mmol), and a catalytic amount of 4-dimethylamino-pyridine. The mixture was stirred at room temperature for 45 minutes and then diluted 100 fold with EtOAc. The organics were washed with H$_2$O, saturated NaHCO$_3$, brine, and concentrated, in vacuo. The crude residue was purified by flash chromatography (SiO$_2$, 10% MeOH in CHCl$_3$), giving 77 mg (90%) of the desired product.

$^1$H NMR(CDCl$_3$) δ9.21 (s, 1H), 7.66 (d, J=8.3 Hz, 2H), 7.37 (m, 10H), 6.99 (dd, J=8.8, 2.0 Hz, 1H), 6.73 (d, J=7.6 Hz, 1H), 6.65 (s, 1H), 5.41 (d, J=7.9 Hz, 1H), 5.12 (s, 2H), 4.21 (s, 2H), 3.96 (s, 2H), 3.70 (s, 3H), 2.96 (bs, 4H), 2.46 (t, J=6.1 Hz, 2H), 2.23 (m, 1H), 1.94 (bs, 4H), 1.89 (m, 1H), 1.46 (s, 9H), 1.45 (s, 9H); EIMS 820.4.

B. (S)-2-[5-(4-Amino-1,5-dioxo-5-hydroxypentylamino)-phenyl]-6-hydroxy-3-[3-methoxy-4-[(1-pyrrolidinyl)methyl]-benzyl]benzo[b]thiophene Dihydrochloride To 70 mg (0.085 mmol) of the above benzyl ether in MeOH (3 mL) was added NH$_4$CO$_2$H (53 mg, 0.850 mmol), 10% Pd/C (70 mg), and the mixture heated at reflux for 25 minutes. The solution was allowed to cool to room temperature and the catalyst removed by filtration over a pad of diatomaceous earth. The filtrate was concentrated, in vacuo, and the resulting residue partitioned between EtOAc and saturated NaHCO$_3$. The organic layer was then washed with H$_2$O, brine, and concentrated, in vacuo. The resulting residue was taken up with TFA, stirred at room temperature for 1 h, then concentrated, in vacuo. After trituration with Et$_2$O, the TFA salt was converted to the HCl salt by dissolving in 0.1 N HCl, freezing and lyophilizing to afford the title product as its dihydrochloride.

$^1$H NMR (CD$_3$OD) δ7.63 (d, J=8.4 Hz, 2H), 7.39 (m, 3H), 7.26 (d, J=7.7 Hz, 1H), 7.19 (d, J=2.0 Hz, 1H), 6.85 (s, 1H), 6.76 (m, 2H), 4.27 (s, 2H), 4.25 (s, 2H), 4.09 (t, J=5.8 Hz, 1H), 3.76 (s, 3H), 3.44 (m, 2H), 3.16 (m, 3H), 2.70 (t, J=7.1 Hz, 2H), 2.26 (m, 2H), 2.09 (m, 2H), 2.00 (m, 2H); FAB MS 574.1 (M+1).

What is claimed is:

1. A compound of formula I (or a pharmaceutically acceptable salt thereof)

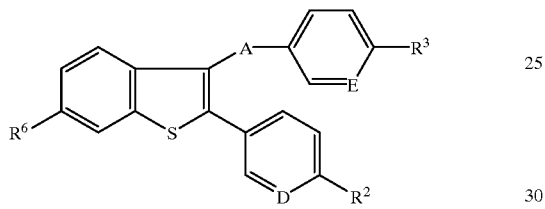

I wherein

A is carbonyl or methylene;

D is CH, CR$^d$ or N in which R$^d$ is methyl or methoxy;

E is CH, CR$^e$ or N in which R$^e$ is methyl, methoxy or halo;

R$^2$ and R$^3$ are defined together such that

A. R$^2$ is —X$^2$—(CH$_2$)$_m$—NR$^a$R$^b$ in which X$^2$ is a direct bond, methylene or O; m is 1, 2, 3, 4 or 5; provided that when m is 1, then X$^2$ is a direct bond; and R$^a$ and R$^b$ are independently hydrogen or (1–3C)alkyl or the group NR$^a$R$^b$ is pyrrolidino, piperidino, or morpholino; and R$^3$ is —CH$_2$—R$^c$, in which R$^c$ is 2-carboxypyrrolidin-1-yl or 2-[[(1–4C)alkoxy]carbonyl]pyrrolidin-1-yl; or B. R$^2$ is —X$^2$—(CH$_2$)$_n$—R$^f$ in which X$^2$ is a direct bond, methylene or O; n is 1, 2 or 3; provided that when n is 1, then X$^2$ is a direct bond; and R$^f$ is 2-carboxypyrrolidin-1-yl, 2-[[(1–4C)alkoxy]carbonyl]pyrrolidin-1-yl, (carboxymethyl)amino, [[(1–4C)alkoxy]carbonylmethyl]amino, (4-carboxymethylimidazol-1-yl)amino, [4-[[(1–4C)alkoxy]-carbonylmethyl]imidazol-1-yl]amino, (4-carboxybenzyl)amino, [4-[[(1–4C)alkoxy]carbonyl]benzyl]amino, (3-amino-1,4-dioxo-4-hydroxybutyl)amino or [3-amino-1,4-dioxo-4-[(1–4C)alkoxy]-butyl]amino; or R$^2$ is —X$^2$—(CH$_2$)$_n$—R$^f$ in which X$^2$ is a direct bond; n is 0; and R$^f$ is (3-amino-1,4-dioxo-4-hydroxybutyl)-amino, [3-amino-1,4-dioxo-4-[(1–4C)alkoxy]butyl]amino, (4-amino-1,5-dioxo-5-hydroxypentyl)amino or [4-amino-1,5-dioxo-5-[(1–4C)alkoxy]butyl]amino;

R$^3$ is is —X$^3$—(CH$_2$)$_s$—NR$^g$R$^h$ in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^6$ is hydrogen, hydroxy or methoxy.

2. The compound of formula I (or a pharmaceutically acceptable salt thereof) as claimed in claim 1 wherein A is carbonyl or methylene;

D is CH, CR$^d$ or N in which R$^d$ is methyl or methoxy;

E is CH, CR$^e$ or N in which R$^e$ is methyl, methoxy or halo;

R$^2$ and R$^3$ are defined together such that

A. R$^2$ is —X$^2$—(CH$_2$)$_m$—NR$^a$R$^b$ in which X$^2$ is a direct bond, methylene or O; m is 1, 2, 3, 4 or 5; provided that when m is 1, then X$^2$ is a direct bond; and R$^a$ and R$^b$ are independently hydrogen or (1–3C) alkyl or the group NR$^a$R$^b$ is pyrrolidino, piperidino, or morpholino; and R$^3$ is —CH$_2$—R$^c$, in which R$^c$ is 2-carboxypyrrolidin-1-yl or 2-[[(1–4C)alkoxy]carbonyl]pyrrolidin-1-yl; or B. R$^2$ is —X$^2$—(CH$_2$)$_n$—R$^f$ in which X$^2$ is a direct bond, methylene or O; n is 1 or 2; provided that when n is 1, then X$^2$ is a direct bond; and R$^f$ is 2-carboxypyrrolidin-1-yl, 2-[[(1–4C)alkoxy]carbonyl]pyrrolidin-1-yl, (carboxymethyl)-amino, [[(1–4C)alkoxy]carbonylmethyl]amino, (4-carboxymethylimidazol-1-yl)amino, [4-[[(1–4C)alkoxy]carbonylmethyl]imidazol-1-yl]amino, (4-carboxybenzyl)amino, [4-[[(1–4C)alkoxy]carbonyl]benzyl]amino, (3-amino-1,4-dioxo-4-hydroxybutyl)amino or [3-amino-1,4-dioxo-4-[(1–4C)alkoxy]-butyl]amino; and R$^3$ is is —X$^3$—(CH$_2$)$_s$—NR$^g$R$^h$ in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^6$ is hydrogen, hydroxy or methoxy.

3. The compound (or salt thereof) as claimed in claim 1 or 2 wherein D is CH.

4. The compound (or salt thereof) as claimed in any one of claims 1 or 2 wherein E is CH or CR$^e$ in which R$^e$ is methyl or methoxy.

5. The compound (or salt thereof) as claimed in any one of claims 1 or 2 wherein R$^2$ is —X$^2$—(CH$_2$)$_m$—NR$^a$R$^b$ in which X$^2$ is a direct bond or O; m is 2; and the group NR$^a$R$^b$ is pyrrolidino; and R$^3$ is —CH$_2$—R$^c$, in which R$^c$ is 2-carboxypyrrolidin-1-yl.

6. The compound (or salt thereof) as claimed in any one of claims 1 or 2 wherein R$^2$ is —X$^2$—(CH$_2$)$_n$—R$^f$ in which X$^2$ is a direct bond or O; n is 2; and R$^f$ is 2-carboxypyrrolidin-1-yl or 2-{{(1–4C)alkoxy}-carbonyl}pyrrolidin-1-yl; and R$^3$ is pyrrolidinomethyl, morpholinomethyl or 2-pyrrolidinoethoxy.

7. The compound (or salt thereof) as claimed in claim 1, wherein R$^2$ is —X$^2$—(CH$_2$)$_n$—R$^f$ in which X$^2$ is a direct bond; n is 0; and R$^f$ is (3-amino-1,4-dioxo-4-hydroxy-butyl) amino or (4-amino-1,5-dioxo-5-hydroxypentyl)amino; and R$^3$ is pyrrolidinomethyl, morpholinomethyl or 2-pyrrolidinoethoxy.

8. The compound (or salt thereof) as claimed in any one of claims 1 or 2 wherein R$^6$ is hydroxy.

9. The compound (or salt thereof) as claimed in any one of claims 1 or 2 wherein A is methylene.

10. The compound as claimed in claim 1 selected from (a) 6-hydroxy-2-[4-[2-[2-(S)-(carboxy)pyrrolidin-1-yl]ethoxy]phenyl]benzo[b]thiophen-3-yl 3-methoxy-4-[(4-morpholinyl)methyl]phenyl ketone, (b) 2-[4-[2-[2-(S)-(tert-butoxycarbonyl)-pyrrolidin-1-yl]ethoxy]phenyl]-6-hydroxy-3-[3-methoxy-4-[(4-morpholinyl)methyl]benzyl]benzo[b]thiophene, and (c) 6-hydroxy-3-[4-[[2-(S)-(hydroxycarbonyl)-pyrrolidin-1-yl]methyl]-3-(methyl)benzyl]-2-[4-[2-(1-pyrrolidinyl)ethoxy]phenyl]benzo[b]thiophene;

or a pharmaceutically acceptable salt thereof.

11. The compound as claimed in claim 1 selected from
(i) (S)-2-[4-(3-amino-1,4-dioxo-4-hydroxybutyl-amino)phenyl]-6-hydroxy-3-[3-methoxy-4-[(1-pyrrolidinyl)methyl]benzyl]benzo[b]thiophene and
(ii) (S)-2-[5-(4-amino-1,5-dioxo-5-hydroxypentyl-amino)phenyl]-6-hydroxy-3-[3-methoxy-4-[(1-pyrrolidinyl)methyl]benzyl]benzo[b]thiophene,
or a pharmaceutically acceptable salt thereof.

12. The compound (or salt thereof) as claimed in claim 1 in which halo is fluoro, chloro, bromo or iodo and a (1–4C)alkoxy group is methoxy, ethoxy, isopropoxy or t-butoxy.

13. The salt as claimed in claim 1 which is an acid-addition salt made with an acid which provides a pharmaceutically acceptable anion.

14. A pharmaceutical formulation comprising in association with a pharmaceutically acceptable carrier, diluent or excipient, a compound of formula I (or a pharmaceutically acceptable salt thereof) as provided in claim 1.

15. A method of inhibiting thrombin comprising using an effective amount of a thrombin inhibiting compound of formula I (or a pharmaceutically acceptable salt thereof) as claimed in claim 1.

16. A process for preparing a novel compound of formula I (or a pharmaceutically acceptable salt thereof) as claimed in claim 1 which is selected from (a) for a compound of formula I in which $R^c$ is 2-[[(1–4C)alkoxy]carbonyl]pyrrolidin-1-yl, alkylating 2-[[(1–4C)alkoxy]carbonyl]pyrrolidine using a compound corresponding to a compound of formula I but in which $R^c$ is a leaving group;

(b) for a compound of formula I in which $R^2$ is —$X^2$—$(CH_2)_n$—$R^f$ in which n is not 0 and the atom joining $R^f$ to —$X^2$—$(CH_2)_n$— is a basic nitrogen, alkylating a corresponding amine of formula H-$R^f$ using a compound corresponding to a compound of formula I but in which $R^f$ is a leaving group;

(c) for a compound of formula I in which $R^2$ is —$X^2$—$(CH_2)_n$—$R^f$ in which n is not 0 and the atom joining $R^f$ to —$X^2$—$(CH_2)_n$— is a basic imino group joined to a methylene group (—NH—$CH_2$—), reductively alkylating a compound corresponding to a compound of formula I but in which $R^f$ is an amino group using the requisite aldehyde;

(d) for a compound of formula I in which $R^2$ is —$X^2$—$(CH_2)_n$—$R^f$ in which n is not 0 and the atom joining $R^f$ to —$X^2$—$(CH_2)_n$— is an amide nitrogen, acylating a compound corresponding to a compound of formula I but in which $R^f$ is an amino group using the requisite acid or an activated derivative thereof;

(e) for a compound of formula I in which $R^2$ is —$X^2$—$(CH_2)_n$—$R^f$ in which n is 0, acylating a compound corresponding to a compound of formula I but in which $R^2$ is an amino group using the requisite acid or an activated derivative thereof;

(f) for a compound of formula I in which $R^2$ or $R^3$ contains a carboxy group, decomposing the ester of a corresponding compound of formula I in which $R^2$ or $R^3$ contains a [(1–4C)alkoxy]carbonyl group;

(g) for a compound of formula I in which A is methylene, reductively removing the hydroxy group of a corresponding alcohol of formula II;

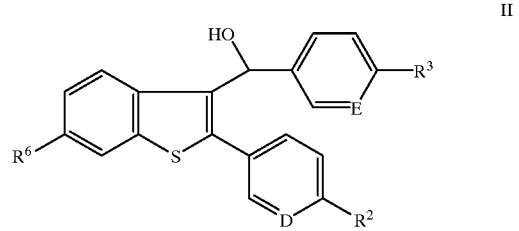

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure;

and wherein, unless otherwise described, A, D, E, $R^2$, $R^3$ and $R^6$ have the values described in claim 1.

17. The compound (or salt thereof) as claimed in claim 3 wherein E is CH or $CR^e$ in which $R^e$ is methyl or methoxy.

18. The compound (or salt thereof) as claimed in claim 3 wherein $R^2$ is —$X^2$—$(CH_2)_m$—$NR^aR^b$ in which $X^2$ is a direct bond or O; m is 2; and the group $NR^aR^b$ is pyrrolidino; and $R^3$ is —$CH_2$—$R^c$, in which $R^c$ is 2-carboxy-pyrrolidin-1-yl.

19. The compound (or salt thereof) as claimed in claim 4 wherein $R^2$ is —$X^2$—$(CH_2)_m$—$NR^aR^b$ in which $X^2$ is a direct bond or O; m is 2; and the group $NR^aR^b$ is pyrrolidino; and $R^3$ is —$CH_2$—$R^c$, in which $R^c$ is 2-carboxy-pyrrolidin-1-yl.

20. The compound (or salt thereof) as claimed in claim 3 wherein $R^2$ is —$X^2$—$(CH_2)_n$—$R^f$ in which $X^2$ is a direct bond or O; n is 2; and $R^f$ is 2-carboxy-pyrrolidin-1-yl or 2-[[(1–4C)alkoxy]carbonyl]pyrrolidin-1-yl; and $R^3$ is pyrrolidinomethyl, morpholinomethyl or 2-pyrrolisinoethoxy.

21. The compound (or salt thereof) as claimed in claim 4 wherein $R^2$ is —$X^2$—$(CH_2)_n$—$R^f$ in which $X^2$ is a direct bond or O; n is 2; and $R^f$ is 2-carboxy-pyrrolidin-1-yl or 2-[[(1–4C)alkoxy]carbonyl]pyrrolidin-1-yl; and $R^3$ is pyrrolidinomethyl, morpholinomethyl or 2-pyrrolisinoethoxy.

22. The compound (or salt thereof) as claimed in claim 3 wherein $R^2$ is —$X^2$—$(CH_2)_n$—$R^f$ in which $X^2$ is a direct bond; n is 0; and $R^f$ is (3-amino-1,4-dioxo-4-hydroxybutyl)amino or (4-amino-1,5-dioxo-5-hydroxy-pentyl)amino; and $R^3$ is pyrrolidinomethyl, morpholinomethyl or 2-pyrrolidinoethoxy.

23. The compound (or salt thereof) as claimed in claim 4 wherein $R^2$ is —$X^2$—$(CH_2)_n$—$R^f$ in which $X^2$ is a direct bond; n is 0; and $R^f$ is (3-amino-1,4-dioxo-4-hydroxybutyl)amino or (4-amino-1,5-dioxo-5-hydroxy-pentyl)amino; and $R^3$ is pyrrolidinomethyl, morpholinomethyl or 2-pyrrolidinoethoxy.

24. The compound (or salt thereof) as claimed in claim 3 wherein $R^6$ is hydroxy.

25. The compound (or salt thereof) as claimed in claim 4 wherein $R^6$ is hydroxy.

26. The compound (or salt thereof) as claimed in claim 17, wherein $R^6$ is hydroxy.

27. The compound (or salt thereof) as claimed in claim 5 wherein $R^6$ is hydroxy.

28. The compound (or salt thereof) as claimed in claim 18 wherein $R^6$ is hydroxy.

29. The compound (or salt thereof) as claimed in claim 19 wherein $R^6$ is hydroxy.

30. The compound (or salt thereof) as claimed in claim 6 wherein $R^6$ is hydroxy.

31. The compound (or salt thereof) as claimed in claim 20 wherein $R^6$ is hydroxy.

32. The compound (or salt thereof) as claimed in claim 21 wherein $R^6$ is hydroxy.

33. The compound (or salt thereof) as claimed in claim 7 wherein $R^6$ is hydroxy.

34. The compound (or salt thereof) as claimed in claim 22 wherein $R^6$ is hydroxy.

35. The compound (or salt thereof) as claimed in claim 23 wherein $R^6$ is hydroxy.

36. The compound (or salt thereof) as claimed in claim 3 wherein A is methylene.

37. The compound (or salt thereof) as claimed in claim 4 wherein A is methylene.

38. The compound (or salt thereof) as claimed in claim 17 wherein A is methylene.

39. The compound (or salt thereof) as claimed in claim 5 wherein A is methylene.

40. The compound (or salt thereof) as claimed in claim 18 wherein A is methylene.

41. The compound (or salt thereof) as claimed in claim 19 wherein A is methylene.

42. The compound (or salt thereof) as claimed in claim 6 wherein A is methylene.

43. The compound (or salt thereof) as claimed in claim 20 wherein A is methylene.

44. The compound (or salt thereof) as claimed in claim 21 wherein A is methylene.

45. The compound (or salt thereof) as claimed in claim 7 wherein A is methylene.

46. The compound (or salt thereof) as claimed in claim 22 wherein A is methylene.

47. The compound (or salt thereof) as claimed in claim 23 wherein A is methylene.

* * * * *